US011049598B2

(12) United States Patent
Weng

(10) Patent No.: US 11,049,598 B2
(45) Date of Patent: Jun. 29, 2021

(54) ROBUST HEALTH TRACKING SERVICE

(71) Applicant: Tricella Inc., Mountain View, CA (US)

(72) Inventor: Daniel M. Weng, Mountain View, CA (US)

(73) Assignee: Tricella Inc., Mountain View, CA (US)

( * ) Notice: Subject to any disclaimer, the term of this patent is extended or adjusted under 35 U.S.C. 154(b) by 471 days.

(21) Appl. No.: 15/368,400

(22) Filed: Dec. 2, 2016

(65) Prior Publication Data

US 2017/0169185 A1 Jun. 15, 2017

Related U.S. Application Data

(60) Provisional application No. 62/266,854, filed on Dec. 14, 2015.

(51) Int. Cl.
| | | |
|---|---|---|
| *G16H 20/10* | (2018.01) | |
| *G16H 40/67* | (2018.01) | |
| *G16H 20/17* | (2018.01) | |
| *G16H 80/00* | (2018.01) | |

(Continued)

(52) U.S. Cl.
CPC ......... *G16H 20/10* (2018.01); *G06Q 10/1093* (2013.01); *G16H 20/17* (2018.01); *G16H 40/63* (2018.01); *G16H 40/67* (2018.01); *G16H 80/00* (2018.01)

(58) Field of Classification Search
CPC ......... G06F 19/3456; A61J 7/04; A61J 7/049; G16H 20/10; G16H 20/13; G16H 40/67; G16H 20/17; G16H 80/00; G16H 40/63; G06Q 10/1093
See application file for complete search history.

(56) References Cited

U.S. PATENT DOCUMENTS

| 6,771,174 | B2 | 8/2004 | Broas |
|---|---|---|---|
| 7,785,895 | B2 | 8/2010 | Larson et al. |
| 9,889,068 | B1 * | 2/2018 | Bakhoum ................. A61J 1/03 |

(Continued)

FOREIGN PATENT DOCUMENTS

| CN | 101947192 A | 1/2011 |
|---|---|---|
| CN | 201701481 U | 1/2011 |

(Continued)

OTHER PUBLICATIONS

Hsu et al., A WSN Smart Medication System, Sep. 8, 2010, Procedia Engineering, pp. 588-591. (Year: 2010).*

(Continued)

*Primary Examiner* — Christopher L Gilligan
(74) *Attorney, Agent, or Firm* — Fenwick & West LLP

(57) ABSTRACT

A solution is provided to monitor and to analyze a user's medicine consumption related to a prescribed therapeutic regimen or a prescribed medication anywhere and anytime through a variety of sensors attached to a health tracking device, e.g., a pillbox. A health tracking service analyzes the sensor data collected by the sensors of the pillbox, e.g., by correlating the sensor data with selected historical health data of the user, and generating health related suggestions for the user based on the correlation. The analysis, recommendations and instructions are presented in a user friendly way to users on users' various consumer electronic devices, such as computers, mobile devices, television sets, and any other suitable electronic devices.

20 Claims, 19 Drawing Sheets

(51) Int. Cl.
*G16H 40/63* (2018.01)
*G06Q 10/10* (2012.01)

(56) References Cited

U.S. PATENT DOCUMENTS

| | | | |
|---|---|---|---|
| 2002/0097156 | A1 | 7/2002 | Broas |
| 2004/0130450 | A1 | 8/2004 | Kleinschmidt |
| 2007/0016443 | A1* | 1/2007 | Wachman ............ G06F 19/3456 705/2 |
| 2007/0272583 | A1 | 11/2007 | Kulkarni |
| 2009/0015245 | A1* | 1/2009 | Burrows ................ A61J 7/0481 324/207.2 |
| 2009/0134181 | A1* | 5/2009 | Wachman ............ G06F 19/3462 221/8 |
| 2012/0038226 | A1* | 2/2012 | Tran .................... G06F 19/3462 307/116 |
| 2012/0072231 | A1 | 3/2012 | Mayer et al. |
| 2012/0248134 | A1* | 10/2012 | Santmyer ................ G07F 17/14 221/1 |
| 2012/0284969 | A1* | 11/2012 | Fullerton .............. H01F 13/003 24/303 |
| 2012/0299731 | A1 | 11/2012 | Triener |
| 2015/0235004 | A1 | 8/2015 | Shor et al. |
| 2015/0278475 | A1 | 10/2015 | Shor |
| 2015/0283036 | A1* | 10/2015 | Aggarwal ................. A61J 7/04 206/534 |
| 2016/0074284 | A1* | 3/2016 | Despa ................... A61J 7/0409 340/573.1 |

FOREIGN PATENT DOCUMENTS

| | | |
|---|---|---|
| CN | 104188806 A | 12/2014 |
| CN | 104970965 A | 10/2015 |
| JP | H09237395 | 9/1997 |
| JP | 2010-170504 A | 8/2010 |
| WO | WO 2006/092999 A1 | 9/2006 |

OTHER PUBLICATIONS

PCT International Search Report and Written Opinion, PCT Application No. PCT/US16/64811, dated Mar. 31, 2017, 18 pages.
Patent Classification, CPC Definition, CPC—A61J—Jan. 2017, 44 pages, 2017, May be Retrieved at<URL:http://www.uspto.gov/web/patents/classification/cpc/html/defA61J.html>.
"The Pillbox Just Got Smarter," Dec. 1, 2015, XP055590978, Retrieved from the Internet: URL:http//webarchive.org/web/20151201014338/https://www.tricella.com/ [retrieved on May 22, 2019].
Extended European Search Report, European Patent Application No. 16876380.3, dated Jun. 6, 2019, 12 pages.
First Chinese Office Action (with English concise explanation of relevance), Chinese Patent Application No. 20168008185.4, dated May 31, 2019, 12 pages.
Second Chinese Office Action, China National Intellectual Property Administration Patent Application No. 20168008185.4, dated Mar. 5, 2020, 26 pages.
Third Chinese Office Action, China National Intellectual Property Administration Patent Application No. 20168008185.4, dated Aug. 14, 2020, 13 pages.
Japanese Office Action, Japan Patent Office Application No. 2018-532278, dated Nov. 10, 2020, sixteen pages.
Suzuki, S. et al., "Medication Management Using Home Sensor Network Toward Home Health Care (Proving test in home care)," IPSJ SIG Technical Report, Heisei-22 (4), [CD-ROM], vol. 2010-UBI-28, No. 20, pp. 1-8, Information Processing Society of Japan, Japan, Dec. 15, 2010, with English abstract.

* cited by examiner

Assessment

How are you feeling (1-5, 1 being the worst)?

[ 2 ] 1520

[ Next ]

Assessment

What is bothering you?

⊗ Pain
○ Depression
○ Anxiety
○ Other, please specify: [_____]

1540

1550

[ Next ]

Assessment

Where does it hurt?
- ⊗ Shoulder
- ○ Stomach
- ○ Left chest
- ○ Other, please specify: ____

1570

1550

1560

[Next]

FIG. 15D

Assessment

Do you want to schedule a doctor appointment?
- ⊗ Yes
- ○ No

1590

1580

[Next]

ROBUST HEALTH TRACKING SERVICE

CROSS-REFERENCE TO RELATED APPLICATION

This application claims the benefit of U.S. Provisional Application No. 62/266,854, filed Dec. 14, 2015, which is incorporated by reference in its entirety.

BACKGROUND

This disclosure relates generally to digital content processing, and particularly to a robust health tracking service that tracks and monitors the consumption of pills (e.g., medication and health supplements) by users of the health tracking service.

Therapeutic non-adherence has been one of the leading causes of hospitalization in patients and deterioration of health for many people. Unfortunately, most people that are not institutionalized or have no on-site professional care services may have a hard time adhering to a prescribed therapeutic regimen or a prescribed medication.

One existing solution is to manually track and monitor a patient's medicine consumption related to a prescribed therapeutic regimen or a prescribed medication. However, manual tracking and monitoring are prone to human errors, e.g., missing or incorrect records of consumption data. Moreover, existing solutions only offer numerical data points in which users must draw conclusions based on their best knowledge. Unfortunately, many people may not have the knowledge on how to interpret the data to make sense of what is presented to them. This can lead to a misunderstanding of information resulting in improper life style arrangements that may decrease the quality of life of the user.

Furthermore, handheld devices, such as mobile devices and tablet computers, have become increasingly popular. The increased availability and bandwidth of network access—for wired and wireless networks—have enabled more communication platforms for digital content consumption and sharing, such as remotely monitoring electronic monitoring devices by mobile devices and sharing information with others on social networking platforms. Thus, manually recording and monitoring medicine consumption without making use of the advancement of mobile technologies is inefficient and ineffective.

SUMMARY

Embodiments of the invention provides a solution to efficiently monitor and to analyze a user's medicine consumption related to a prescribed therapeutic regimen or a prescribed medication anywhere and anytime through a variety of sensors attached to a health tracking device. The analysis, recommendations and instructions are presented in a user friendly way to users on users' various consumer electronic devices, such as computers, mobile devices, television sets, and any other suitable electronic devices.

In one embodiment, a health tracking device, e.g., a pillbox, has one or more sensors embedded in the device, multiple bins and a communication component. The one or more sensors are configured to record events based on the user opening or closing one or more bins of the device; the multiple bins are configured to store medicine pills related to the user's health; and the communication component is configured to transmit the recorded sensor data to a health tracking service and to received information from the health tracking device. The one or more sensors of the health tracking device include a magnetic sensor configured to record an event when the state of a switch associated with a bin of the pillbox changes, and the event indicating whether the bin of the pillbox was opened or closed; an optical sensor configured to detect displacement of a bin of the pillbox with respect to an outer housing of the pillbox to detect whether the bin was opened or closed; a conductive sensor configured to detect that a bin of pillbox was opened in response to a conductive patch embedded with the bin detaching from the conductive sensor; a pressure sensor configured to detect whether content is present in a bin of the pillbox in response to the state of a switch associated with the bin changes; and a volume sensor configured to detect whether there is a change in volume of content present in a bin of the pillbox based on difference between a first volume of the bin and a second volume of the bin, the first volume of the bin being recorded when the bin was empty and the second volume of the bin being recorded when the bin contains content.

The solution includes a health tracking service which provides recommendations and instructions based on analysis of the recorded sensor data of the user and presents the recommendations and instructions in a user friendly way to users on users' various consumer electronic devices. In one embodiment, the health tracking service receives the recorded sensor data collected by the sensors of the pillbox, correlates the sensor data with selected historical health data of the user, e.g., by applying a trained model to the received data, and generates health related suggestions for the user based on the correlation. For example, the health tracking service compares the analysis data of the user's medicine consumption derived from the collected sensor data with the user input data (e.g., daily doses of the prescribed medicine from the user's family doctor), and determines error in dispensing by detecting a discrepancy between scheduled activities versus actual user behavior. If the analysis data does not match the user input data, the health tracking service provides warning of accidental or abuse of medicine dispensation and provides notifications to the user's client device or to other authorized recipients' client devices.

BRIEF DESCRIPTION OF THE DRAWINGS

FIG. 15A-FIG. 15D show examples of a graphical user interface for presenting a risk assessment questionnaire on a client device for a user to input answers to the questionnaire according to one embodiment.

The figures depict various embodiments of the present invention for purposes of illustration only. One skilled in the art will readily recognize from the following discussion that alternative embodiments of the structures and methods illustrated herein may be employed without departing from the principles of the invention described herein.

DETAILED DESCRIPTION

System Overview

A solution is provided to monitor and to analyze a user's medicine consumption related to a prescribed therapeutic regimen or a prescribed medication anywhere and anytime through a variety of sensors attached to a health tracking device. The analysis, recommendations and instructions are presented in a user friendly way to users on users' various consumer electronic devices, such as computers, mobile devices, television sets, and any other suitable electronic devices. For simplicity, in one embodiment, the content contained in bins (e.g., a variety of containers and chambers of the health tracking device are a user's prescription drugs and health supplemental pills (e.g., vitamins). In other embodiment, the content includes other types of ingestible items, e.g., candies.

Figure 1:
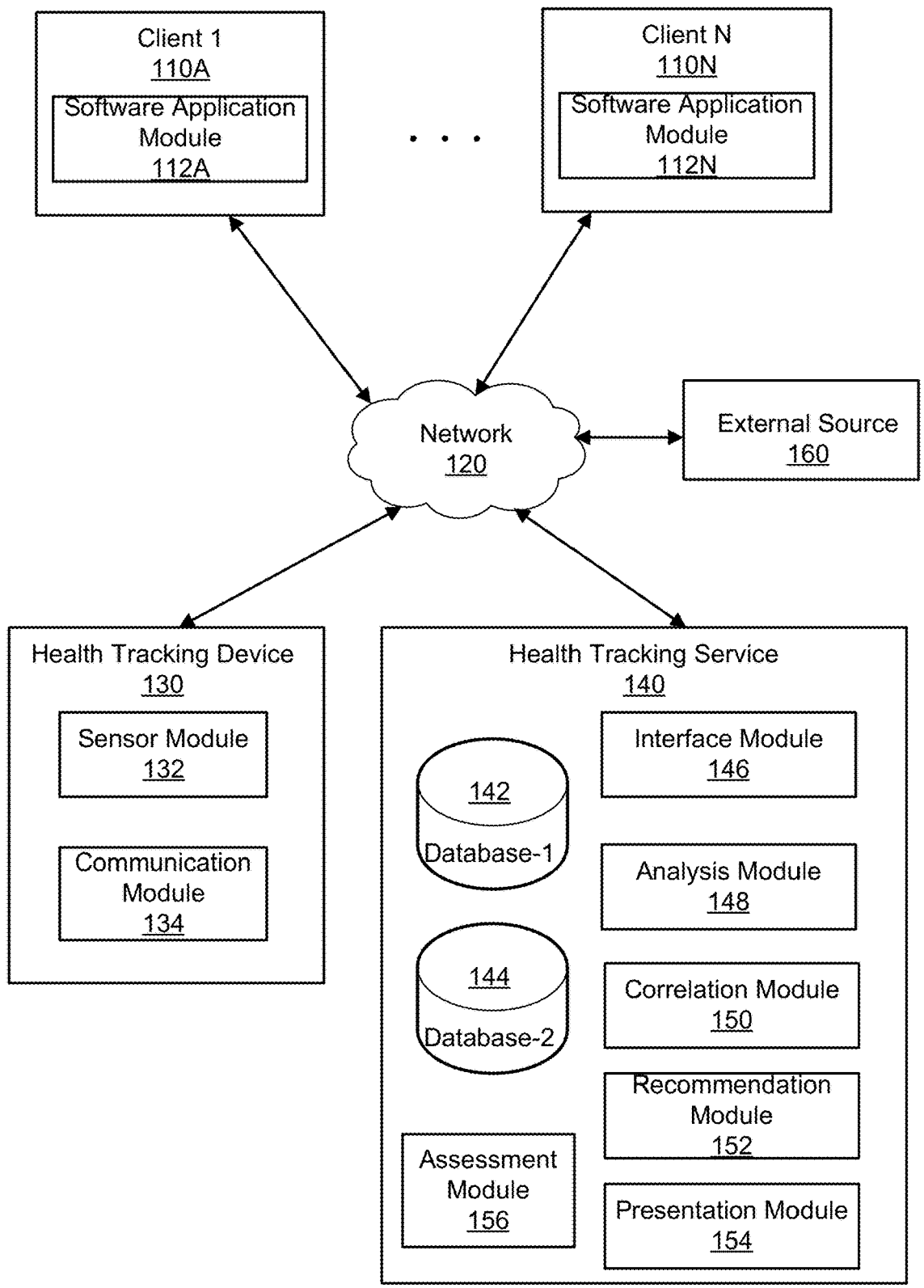
FIG. 1 is a block diagram of a computing environment for monitoring and analyzing a user's medicine consumption according to one embodiment.

FIG. 1 is a block diagram of a computing environment 100 for monitoring and analyzing a user's medicine consumption related to a prescribed therapeutic regimen or a prescribed medication according to one embodiment. The embodiment illustrated in FIG. 1 includes multiple client devices 110 (e.g., 110A and 110N), a health tracking device 130, a health tracking service 140, and an external source 160 connected to each other by a network 120. Embodiments of the computing environment 100 can have many client devices 110, health tracking devices 130, health tracking services 140, and external sources 160 connected to the network 120. Likewise, the functions performed by the various entities of FIG. 1 may differ in different embodiments.

A client device, e.g., 110A, is an electronic device used by a user to perform functions such as tracking a user's medicine consumption related to a prescribed therapeutic regimen or a prescribed medication, executing software applications, consuming digital content, browsing websites hosted by web servers on the network 120, downloading files, and the like. For example, the client device 110 may be a mobile device, a tablet, a notebook, a desktop computer, or a portable computer. The client device 110 includes and/or interfaces with a display device on which the user may view webpages, videos and other content. In addition, the client device 110 provides a user interface (UI), such as physical and/or on-screen buttons with which the user may interact with the client device 110 to perform functions such as viewing, selecting, and consuming digital content such as digital medical records, webpages, photos, videos and other content.

In one embodiment, the client device 110 has a software application module 112 (e.g., 112A for client device 110A and 112N for client device 110N) for executing a software application designed to monitor a user's medicine consumption related to a prescribed therapeutic regimen or a prescribed medication anywhere and anytime. The software application is executed to promote therapeutic adherence in terms of medicine consumption and efficacy of various treatments based on user's behavioral tracking, and to provide input to the health tracking device 130 and the health tracking service 140. For example, upon executing the software application installed in the client device 110, the software application module 112 communicates with the health tracking device 130 and the health tracking service 140 to initiate a monitoring process. A patient has a prescribed therapeutic regimen or a prescribed medication and a user of the client device 110 (e.g., the patient herself or himself, or family, friends, caregivers, practitioners, hospitals, and some combination thereof) can start monitoring medicine consumption associated with the prescribed therapeutic regimen or the prescribed medication. The software application module 112 presents a user friendly interface for a user to input prescription and personal information, and monitoring settings, e.g., medicine type, medicine quantity, medicine strength, medicine taken frequency, remind time, user's medical profile, user's medical demographics, option to order the prescribed medication and so forth. Responsive to recommendations of medicine consumption from the health tracking service 140, the software application module 112 displays the data associated with medicine consumption and recommendations on a display of the client device 110 for the users to digest and share.

The software application module 112 may also present different colors for each bin of the health tracking device 130 to differentiate among contents (e.g., different types of medication) stored in the bins of the health tracking devices and timing information related to a prescribed therapeutic regimen or a prescribed medication. The user of the client device may instruct an external source, e.g., the external source 160 shown in FIG. 1, to export historic data of a patient through the client device to the health tracking service 140 for analysis.

Figure 14A:
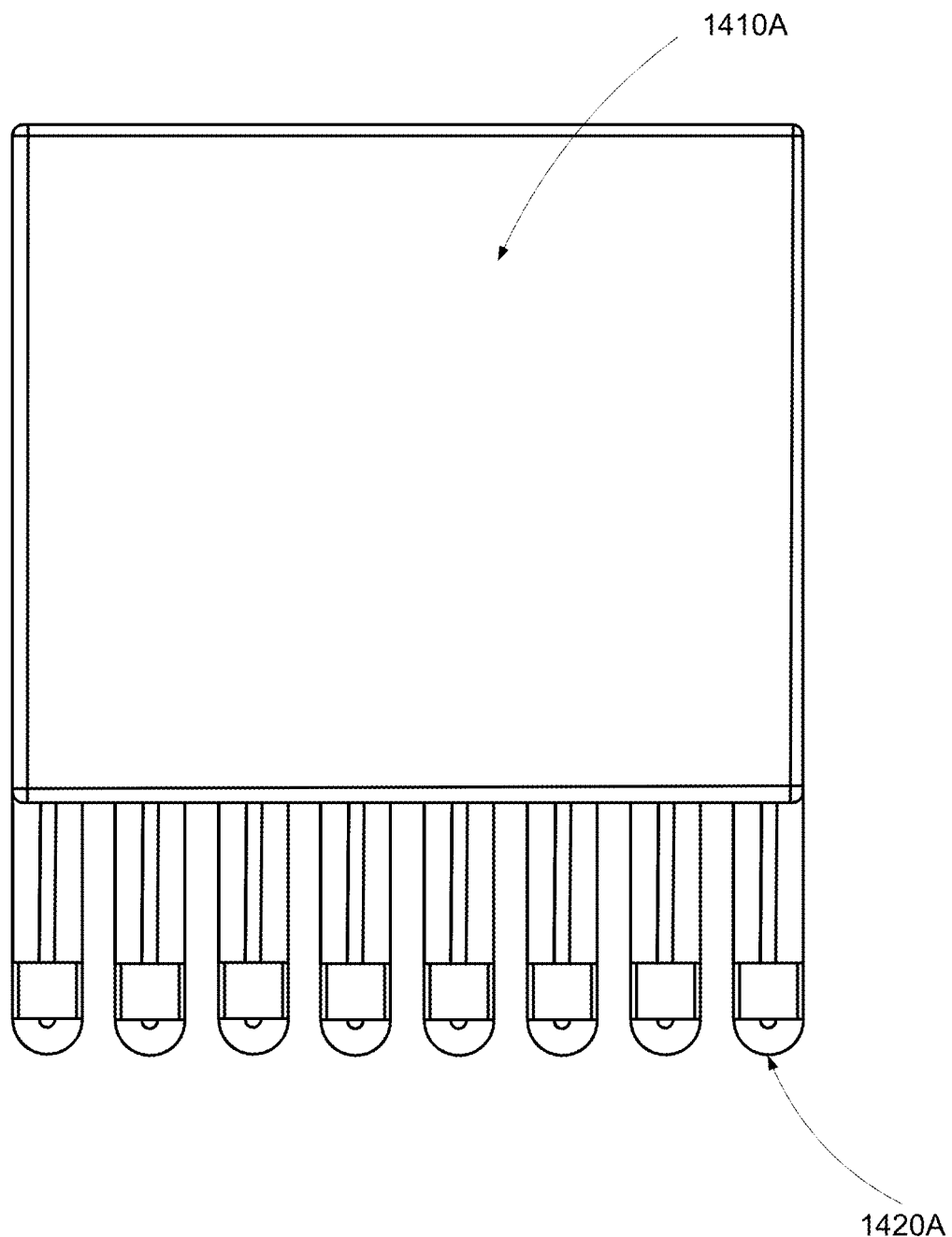
FIG. 14A shows a top view of a health tracking device having multiple bins or containers and a display screen according to another embodiment.
Figure 14B:
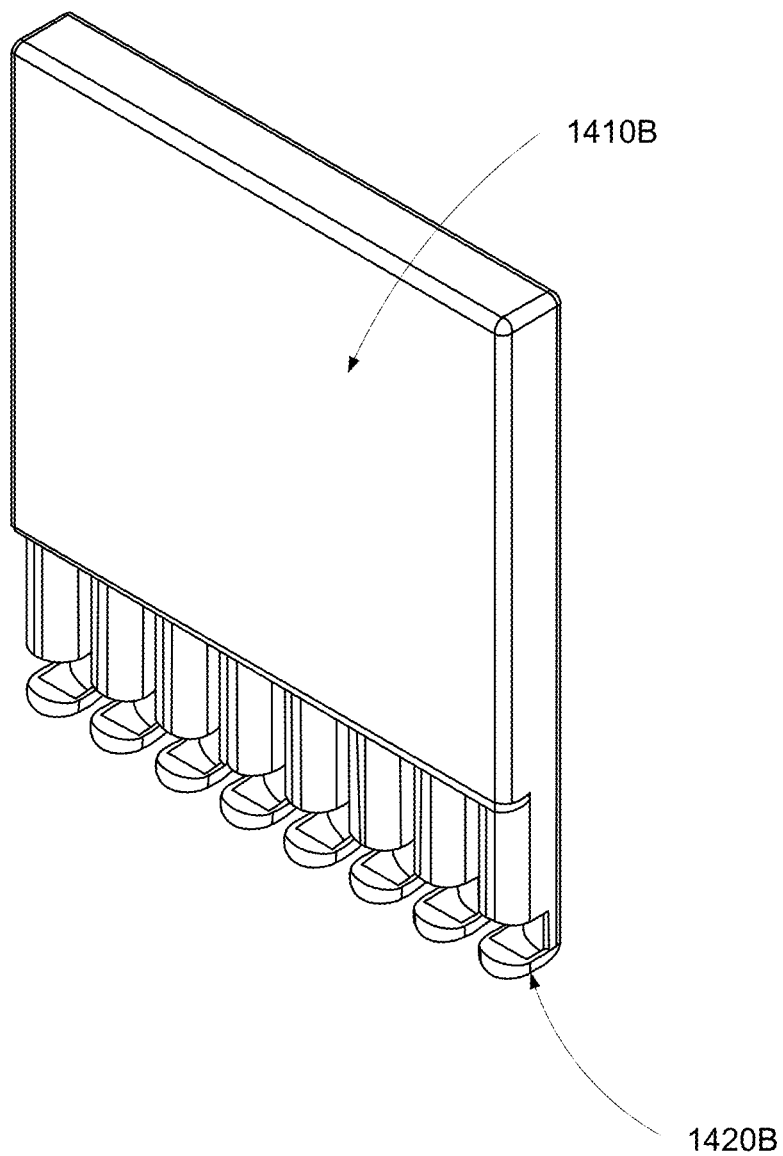
FIG. 14B shows a prospective view of a health tracking device having multiple bins or containers and a display screen according to another embodiment.

The software application module 112 can be similarly installed and executed on computing devices associated with additional caregivers, family members, friends and or qualified practitioners that have been granted permission to participate in monitoring a patient's a prescribed therapeutic regimen or a prescribed medication. The caregivers, family members, friends and qualified practitioners can easily respond and provide instructions to events related to a patient's a prescribed therapeutic regimen or a prescribed medication through one-touch response using a similar user interface. For example, a caregiver can record audio messages from a notification screen of the user interface provided by the corresponding software application module 112. Additionally, a caregiver can send text messages or record a short video that can serve as reminders to the user to promote therapeutic adherence. In some embodiments, the notification messages (e.g., the audio, text and video messages) are displayed on multiple display devices, such as television sets, digital signage, portable display devices or stationary display devices. FIG. 8 through FIG. 12 further illustrate examples of presenting monitoring and recommendation information associated with a user's medicine consumption related to a prescribed therapeutic regimen or a prescribed medication anywhere and anytime on the client device 110. FIG. 14A and FIG. 14B show another embodiment of the health tracking device 130, which has a display screen to display instructions or notification messages from caregivers, family members, friends and or qualified practitioners that have been granted permission to participate in monitoring a patient's a prescribed therapeutic regimen or a prescribed medication.

The network 120 enables communications among network entities such as the client devices 110, the health tracking device 130, the health tracking service 140, and the external source 160. In one embodiment, the network 120 comprises the Internet and uses standard communications technologies and/or protocols, e.g., Bluetooth, WiFi, zigbee, clouding computing, other air to air, wire to air networks, and mesh network protocols to client devices, gateways, access points. In another embodiment, the network entities can use custom and/or dedicated data communications technologies.

The health tracking device 130 collects data associated with a user's medicine consumption related to a prescribed therapeutic regimen or a prescribed medication based on monitoring of status of each bin of the health tracking device 130 through multiple sensors attached to the bins of the health tracking device 130. Based on the collected data, the health tracking device 130 derives information about the user's medicine consumption, e.g., date, time, and frequency of medicine consumption or dispensation; volumes of consumption; errors in medicine dispensation by detecting discrepancy between scheduled activities versus actual user behavior; and so forth. The health tracking device 130 is further described below and with reference to FIG. 2, FIGS. 3A-3C, FIGS. 4A-4D and FIG. 7. FIG. 14A and FIG. 14B show another embodiment of the health tracking device 130, which has a display screen to display a variety of instructions or notification messages regarding the monitoring of a patient's a prescribed therapeutic regimen or a prescribed medication.

The external source 160 aggregates historical health data of a user (e.g., a patient's electronic medical records, or EMRs) from various health record sources (e.g., hospital records, records at the user's family doctors, or manually inputted data related to the user's health). The historical health data of a user describes a global view of the user's lifestyle and wellness. In one embodiment, a user's historical health data is related to various health measurements in terms of activity, ingestion, nourishment, hydration, body weight, biometric data, heart rate, heart rate variability, respiration, blood pressure, quality of sleep and pulse oxygenation. The historical health data of a user can also include information about a user's sodium levels and various nutrients derived from the user's food consumption, and drug adherence related to prescribed therapeutic regimens or prescribed medications.

The health tracking service 140 processes the sensor data collected by the health tracking device 130, provides instructions to the health tracking device 130, and provides recommendations based on the analysis of the sensor data from the health tracking device 130 and historical health data from the external source 160 to the client device 110 for display. The health tracking service 140 is further described below and with reference to FIG. 5 and FIG. 7.

Health Tracking Device

The health tracking device 130 collects data associated with a user's medicine consumption related to a prescribed therapeutic regimen or a prescribed medication based on monitoring of status of each bin of the health tracking device 130 through multiple sensors attached to the bins of the health tracking device 130. In the embodiment illustrated in FIG. 1, the health tracking device 130 includes a sensor module 132 and a communication module 134. The health tracking device 130 also possibly includes other electronics (not shown in FIG. 1), such as a battery (e.g., user replaceable battery, rechargeable battery), a charger (e.g., inductive charging, Pogo pin charging with magnetic plug), radio frequency and wireless transmission, and a system clock (e.g., real time clock). Other embodiments of the health tracking device 130 can include different and/or additional modules other than the ones shown in FIG. 1. For example, the health tracking device 130 may include an analysis module for analyzing the data from the sensor module 132. The sensor module 132 is further described with reference to the description of FIG. 2.

In one embodiment, the health tracking device 130 is a smart pillbox that has a number of bins (e.g., 1 bin, 4 bins, 7 bins, 28 bins, 30 bins or 120 bins) to hold medicine/health supplemental pills and an outer housing to house the bins. The bins and outer housing of the health tracking device can be made of various types of materials and coatings to create a chemical inert barrier. The various materials may be, but not limited to, stainless steel, aluminum, alloy, glass, polyethylene (PE), high-density polyethylene (HDPE), polycarbonates (PC), styrene, acrylonitrile butadiene styrene (ABS), thermoplastic polyurethane (TPU), other food grade poly elastomers or urethanes, or some combination thereof.

In one embodiment, the health tracking device 130 is able to open up all bins simultaneously for ease of use, e.g., medicine loading, sorting or refill. The health tracking device 130 achieves this function by a component (not shown) attached to the health tracking device 130. The component can be an interface fixture controlled by a user. In some embodiments, the component can be controlled by the health tracking service 140 via the communication module 134. In other embodiments, each individual bin of the health tracking device 130 can be opened and closed independently from other bins of the health tracking device 130.

In one embodiment, the health tracking device 130 is used in conjunction with a docking station in which the health tracking device 130 may increase the ease of use for the user to sort medicine pills and place them into the desired bins. In some embodiments, the health tracking device 130 is configured to record inventory of the contents the user is placing into the bins of the health tracking device 130.

Figure 3A:
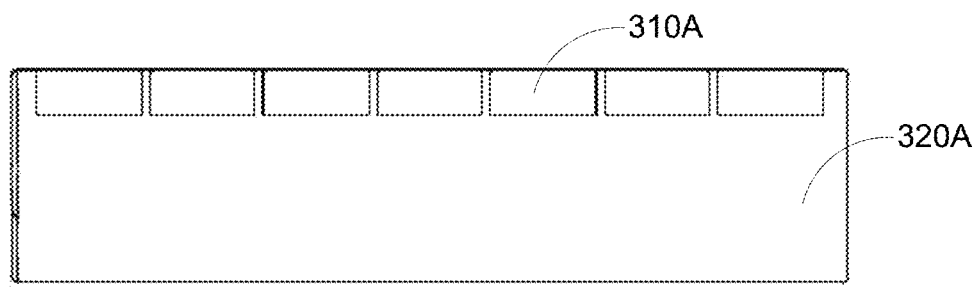
FIG. 3A is a top view of a health tracking device having multiple bins or containers to store medicines according to one embodiment.
Figure 3B:
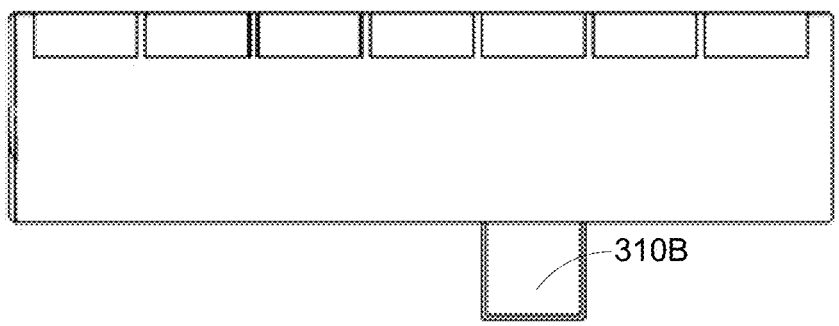
FIG. 3B is a top view of the health tracking device illustrated in FIG. 3A with one bin open according to one embodiment.
Figure 3C:
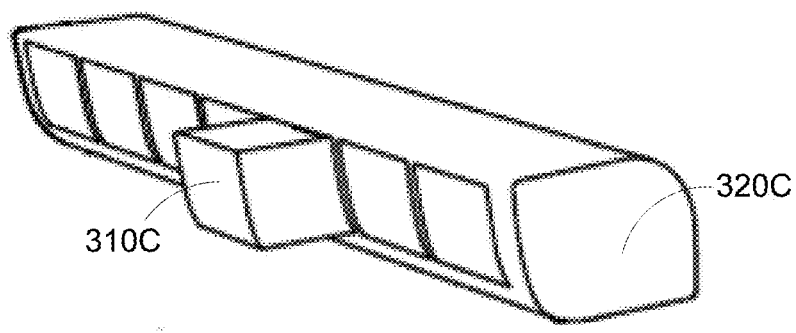
FIG. 3C is a prospective view of the health tracking device illustrated in FIG. 3A with one bin open according to one embodiment.

Turning now to FIGS. 3A-3C, FIGS. 3A-3C show examples of a health tracking device 130 with its corresponding bins in various status. FIG. 3A is a top view of the health tracking device 130 having 7 bins to store medicines according to one embodiment. FIG. 3B is a top view of the health tracking device 130 illustrated in FIG. 3A with one bin (310B) open according to one embodiment. FIG. 3C is a prospective view of the health tracking device 130 illustrated in FIG. 3A with one bin (310C) open according to one embodiment. The bin (310A, 310B, 310C) can be slid into and out of an outer housing (e.g., 320A, 320C). The bin (310A, 310B, 310C) is pushed to open from an opposing side, which is used to increase the ease of use for people with dexterity problems, e.g., arthritis patients. As can be seen from FIG. 3B, the opened bin 310B has an elongated storage that allows contents (e.g., medicine pills) to be removed or dispensed. In one embodiment, each bin has markings to indicate timing information, e.g., day of the week or time of the day, or to indicate types of contents. Moreover, different bins may have different markings. As can be seen from FIG. 3C, the outer housing 320C has an oblong shape with rounding edges. In one embodiment, the outer housing 320C has a different shape, e.g., lobe, or polygon, to prevent rolling on a sloped surface. The top and bottom of the outer housing 320C are flat to prevent rolling. The bottom of the outer housing can have an anti-skid surface to prevent unintentional sliding on a non-level surface as well as a sound dampening element for soft landing (not shown in FIG. 3). In another example (not shown in FIGS. 3A-3C), the bin independently pivots or rotates to dispense contents.

In one embodiment, outer housing (320A, 320C) has water tight seals (e.g., water proof, or dish washer safe) on all the electrical components allows the health tracking device 130 to be cleansed or rinsed with a liquid by the user without damage to its functionality or components.

FIGS. 14A and 14B show examples of a health tracking device 130 with its corresponding bins and a display screen. FIG. 14A is a top view of the health tracking device 130 having 8 bins (e.g., 1420A) to store medicines and a display screen 1410A to display information, instructions and notifications related to tracking of its associated patient's consumption related to a prescribed therapeutic regimen or a prescribed medication according to another embodiment. In one embodiment, the display screen 1410A has a communication interface. FIG. 14B is a prospective view of the health tracking device 130 illustrated in FIG. 14A according to another embodiment. The health tracking device 130 shown in FIG. 14A and FIG. 14B can be flexibly placed on top of a level surface, e.g., a table, or hang vertically against a wall.

Turning back to FIG. 1, the communication module 134 of the health tracking module 130 communicates with the sensor module 132 of the health tracking device 130, and the health tracking service 140. In one embodiment, the communication module 134 receives sensor data from the sensor module 132 and provides the sensor data to the health tracking service 140 for further processing.

The communication module 134 also receives instructions from the health tracking service 140. The instructions may include configurations of the health tracking device 130, and notifications (e.g., warning of accidental or abusive medicine dispensations, reminder for a user to take medication). In one embodiment, the configurations received from the health tracking device 130 may include patient profile, type of the health tracking device (e.g., 4-bin health tracking device, or 7-bin health tracking device), device setting information (e.g., set by medicine type, set by patient, or set by day), medicine information (e.g., medicine type, medicine quantity, expiration/best by date and medicine strength), consumption information (e.g., date, time and frequency of medicine consumption), user input (e.g., user specified time for taking medicine), monitoring participants information (e.g., family, friends, caregivers, practitioners, hospitals), inventory information of contents stored in the bins of the health tracking device 130 (e.g., full, empty, or any other status of the inventory), or any other suitable information affecting the settings of the health tracking device. For example, in response to an instruction of a configuration from the health tracking service 140 that the health tracking device 130 is set by day (e.g., 7 days from Sunday to Saturday for 7-bin health tracking device), the communication module 134 sets the system clock embedded in the health tracking device 130 indicating one bin corresponding to one day, and instructs the system clock to track time for each bin. For another example, in response to an instruction of a warning from the health tracking service 140, the communication module 134 instructs the sensor module 132 to display a warning, e.g., powering on a light emitting diode (LED) in a bin that triggered the warning. Examples of the configuration and notification information of the health tracking device 130 are shown in conjunction with FIGS. 8-10.

In some embodiments, the communication module 134 can also communicate with the software application module 112 of the client device 110 for receiving instructions including the configurations and notifications discussed above. In alternative embodiments, the communication module 134 can also communicate with the software application module 112 of the client device 110 for sending analysis results generated by an analysis module embedded in the health tracking device 130.

In some embodiments, the communication module 134 achieves wireless connectivity that can automatically or manually synchronize data obtained from the health tracking device to a client device, internet based servers or home base stations (gateway). In one example, the communication module 134 is able to transmit data through various wired and/or wireless protocols such as Bluetooth, WiFi, zigbee, other air to air, wire to air networks, mesh network protocols to client devices, gateways, access points, and so forth. In another example, the communication module 134 can also transmit data through near field communication (NFC), which enables the health tracking device 130 to establish radio communication with the client device via touching each other or bringing them into proximity to a distance. In another embodiment, the communication module 134 enables the health tracking device as a wireless range extender via wireless connectivity to synchronize data with a client device, or internet based servers or home base stations.

The communication module 134 also communicates with the client device through wireless pairing. The wireless pairing can be implemented through manual configuration, through a wide area network interface, or a local area network interface via a stationary or a client device. For example, the communication module 134 achieves wireless pairing by several approaches of automatic pairing sequence, e.g., proximity initial paring sequence or optical pattern recognition. Proximity initial paring sequence allows the health tracking device to initiate the pairing sequence via embedded NFC tags by placing the health tracking device in close proximity or by touching the health tracking device to a client device, computer or gateway. The NFC can also initiate pairing sequence for none NFC communications. Optical pattern recognition uses an optical identifier to pair the health tracking device to a client device, computer or gateway. The communication module 134 can also automatically pair the health tracking device within wireless transmission range of a client device, computing device, or gateway.

Figure 2:
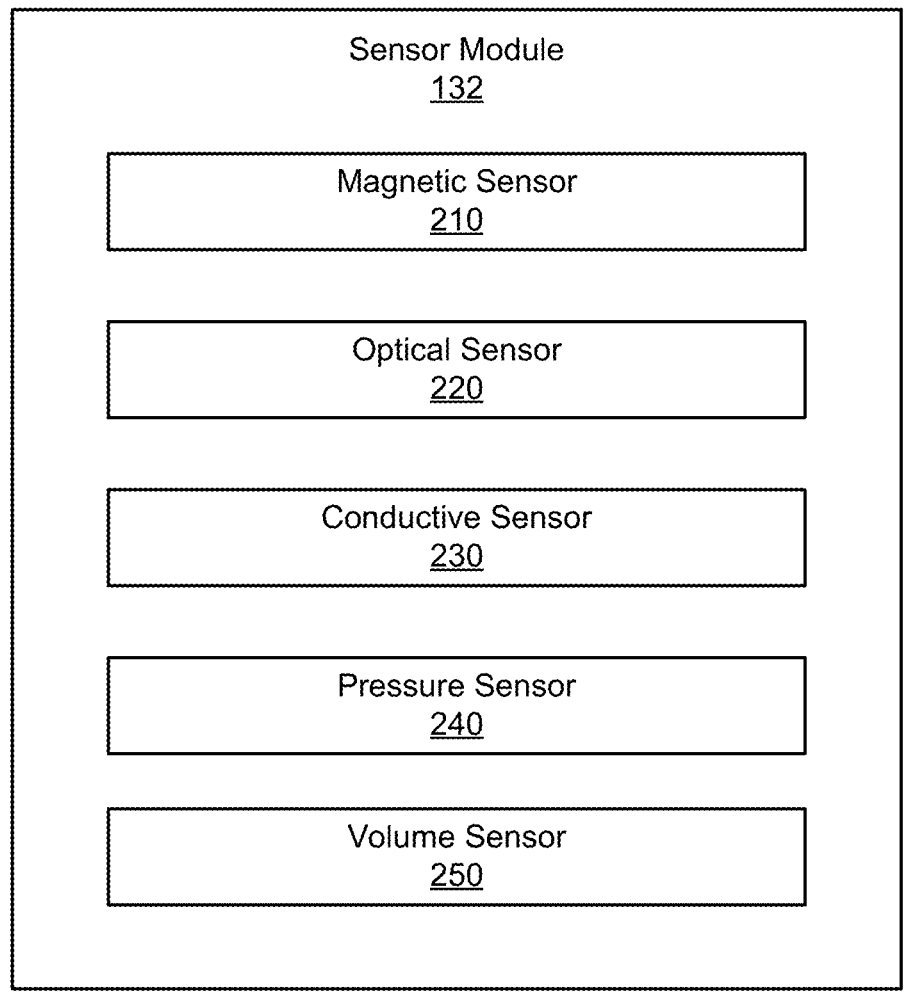
FIG. 2 is a block diagram of a sensor module of a health tracking device to collect sensor data related to a user's medicine consumption according to one embodiment.

The health tracking device 130 collects sensor data through a sensor module 132. FIG. 2 is a block diagram of a sensor module 132 of the health tracking device 130 configured to collect sensor data through various sensors according to one embodiment. The sensor module 132 shown in the embodiment of FIG. 2 includes a magnetic sensor 210, an optical sensor 220, a conductive sensor 230, a pressure sensor 240, and a volume sensor 250. Other embodiments of the sensor module 132 can include different and/or additional sensors. For example, the sensor module 132 can include one or more multi-axis sensors, one or more accelerometers, one or more gyroscopes, one or more magnetometers, and a motion sensor. The sensor module 132 can also include one or more temperature sensors, one or more humidity sensors, or one or more ultraviolet (UV) sensors, another suitable type of sensor that detects the environment of the health tracking device 130, or each bin, or some combination thereof.

The magnetic sensor 210 records an event when the state of a switch associated with a bin of the health tracking device 130 changes. In one embodiment, each bin imbeds one or more magnets. The outer housing of the health tracking device 130, e.g., 320C shown in FIG. 3C, houses the magnetic sensor 210 with a printed circuit board (PCB). In one embodiment, when the magnet in a bin attaches to the magnetic sensor 210 in the outer housing, the magnetic sensor 210 records an event indicating that the bin is closed or open. When the magnet in the bin detaches from the magnetic sensor 210, the magnetic sensor 210 records an event that the bin is open or closed. The PCB supports the magnetic sensor 210 for data transmission, power supply, signal control, or any suitable support or electrical connections. In another embodiment, the magnetic sensor 210 also houses a power cell, circuitry for processing and radio transmission components. In some embodiments, the magnetic sensor 210 records an event when specific conditions are met. For example, the magnetic sensor 210 records an event indicating whether the switch is activated for a duration that is equal or exceeds a predefined time threshold. A system administrator and/or a user of the health tracking device 130 can define or modify a time threshold associated with a switch event detected by the magnetic sensor 210. In some embodiments, the magnetic sensor 210 can be a reed sensor, a hall-effect sensor, or any other suitable sensor that can function as a switch, or a component that is activated by polarity of a magnet or magnetized material.

The optical sensor 220 records an event when the state of a switch associated with a bin of the health tracking device 130 changes and detects if contents (e.g., medicine pills) are present in the bin. In one embodiment, the optical sensor 220 detects displacement of the bin with respect to the outer housing to detect if a bin is open or closed. The optical sensor 220 can also detect difference between the bin being unloaded and the bin being loaded with contents. In one embodiment, the optical sensor 220 includes one or more imaging devices and one or more illumination sources. The imaging device is a device that converts light into electronic signals. The imaging device is capable of measuring changes in light, such as changes related to optical properties of the light (e.g., intensity, phase, polarization, wavelength and spectral distribution). Additionally, the imaging device may detect a change in direction of light. Examples of the imaging device include one or more digital cameras, one or more video cameras, or any other electronic devices capable of capturing images of the bin or the content in the bin. The illumination source can be different types of light sources visible or non-visible in various embodiments. Example light sources include: a light emitted diode (LED), a laser diode, or other type of light emitting device. In some embodiments, the illumination source may be used to compensate for various lighting conditions to prevent false positives that may be triggered by changes in intensity of ambient light. In another embodiment, the illumination source also can be used for displaying a warning.

The conductive sensor 230 (e.g., which can be but not limited to capacitive sensors, including dome switch, toggle switch, etc.) records an event when the state of a switch associated with a bin of the health tracking device 130 changes. In one embodiment, each bin imbeds one or more conductive patches. The outer housing of the health tracking device 130 houses the conductive sensor 230 with a corresponding PCB. In one embodiment, when the conductive patch in the bin detaches from the conductive sensor 230 in the outer housing, the circuit on the PCB is completed via the bin's conductive surface, the conductive sensor 230 records an event indicating that the bin is open. When the conductive patch in the bin attaches to the conductive sensor 230 in the outer housing, the circuit on the PCB is closed, and the conductive sensor 230 detects an event indicating that the bin is closed. In another embodiment, the conductive sensor 230 records an event indicating that the bin is open when the circuit is open, and detects an event indicating that the bin is closed when the circuit is on.

The pressure sensor 240 records an event when the state of a switch associated with a bin of the health tracking device 130 changes and detects if contents are present in the bin. In one embodiment, the pressure sensor 240 includes a pressure switch and a pressure switch. When the pressure switch is activated, the pressure sensor 240 records an event indicating that contents are present in the bin. The pressure sensor 240 can measure the pressure in micro scales. The pressure generated by the contents can be caused by creating a void between two opposing walls of the bins. In another embodiment, the pressure sensor can also measure some characters of the contents in the bin, e.g., weight, volume, or anther suitable character of the content.

The volume sensor 250 detects if there is a change in volume of contents present in each bin of the health tracking device 130. In one embodiment, the volume sensor 250 detects a first volume when the bin is empty and records the first volume as a reference. When the bin is loaded with contents, the volume sensor 250 detects a second volume. If the difference between the first volume and the second volume is equal to or exceeds a threshold value, the volume sensor 250 records an event indicating that content is present in the bin. Similarly, the volume sensor 250 detects a third volume. If the difference between the second volume and the third volume is equal or exceeds another threshold value, the volume sensor 250 records an event indicating that the volume of the content in the bin is changed.

In another embodiment, the sensor module 132 can also include one or more temperature sensors, one or more humidity sensors, or one or more UV sensors that detects the environment of the health tracking device 130, or each bin, or some combination thereof. For example, the humidity sensor of the sensor module 132 monitors the humidity level in each bin. Responsive to the detected humidity level in a bin of the health tracking device 130 exceeding a predetermined threshold value, the humidity sensor determines that the content in the bin may be comprised and records an event indicating that the content in the bin needs evaluation before the content being consumed. Similarly, the temperature sensor of the health tracking device 130 tracks changes of the temperature of the health tracking device 130 or each bin and determines whether the content in the bins of the health tracking device 130 is comprised by the changes of the temperature. A UV sensor of the health tracking device 130 detects ultraviolet radiation projected onto the health tracking device 130 by sunlight, ambient or artificial light or combination of thereof, and determines whether the content in the bin of the health tracking device 130 is comprised, e.g., undesired chemical reactions caused by some long-wavelength in the sunlight over a determined period of time.

Figure 4A:
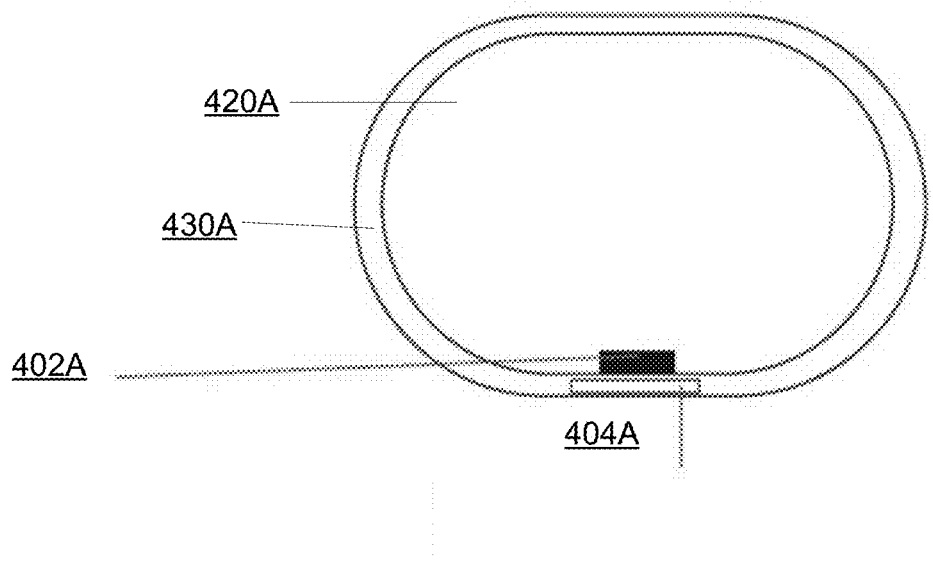
FIG. 4A is an exemplary sensor to detect an event in a health tracking device having a bin closed according to one embodiment.
Figure 4B:
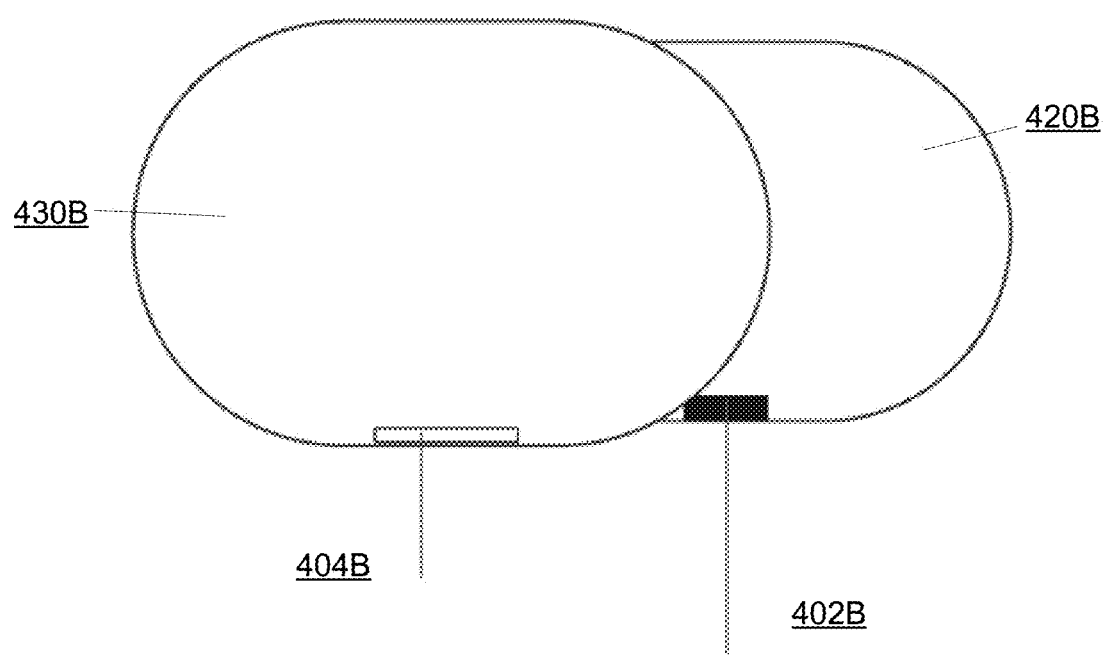
FIG. 4B is an exemplary sensor to detect an event in the health tracking device illustrated in FIG. 4A with a bin open according to one embodiment.

FIGS. 4A-4B show an exemplary sensor to detect an event in the health tracking device 130 in the case of one bin 420 being closed and being open, respectively, according to one embodiment. In this example, 402A and 402B can be a magnet or a conductive patch; accordingly, the 404A, and 404B are a magnetic sensor or a conductive sensor with a corresponding PCB. In another embodiment, 404A and 404B can also be other sensors (e.g., optical sensor, pressure sensor, volume sensor) with their corresponding PCBs. In conjunction with description of FIG. 2, when the bin 420A is closed as shown in FIG. 4A, the magnet or conductive patch 402A attaches to the corresponding sensors 404A.

Figure 4C:
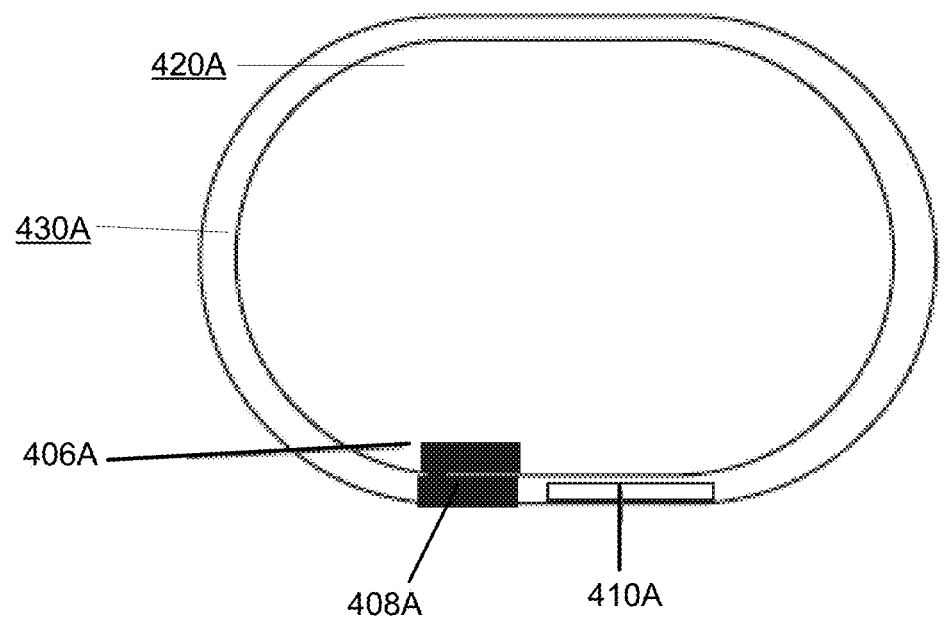
FIG. 4C is an exemplary sensor to detect an event in a health tracking device having a bin closed according to another embodiment.
Figure 4D:
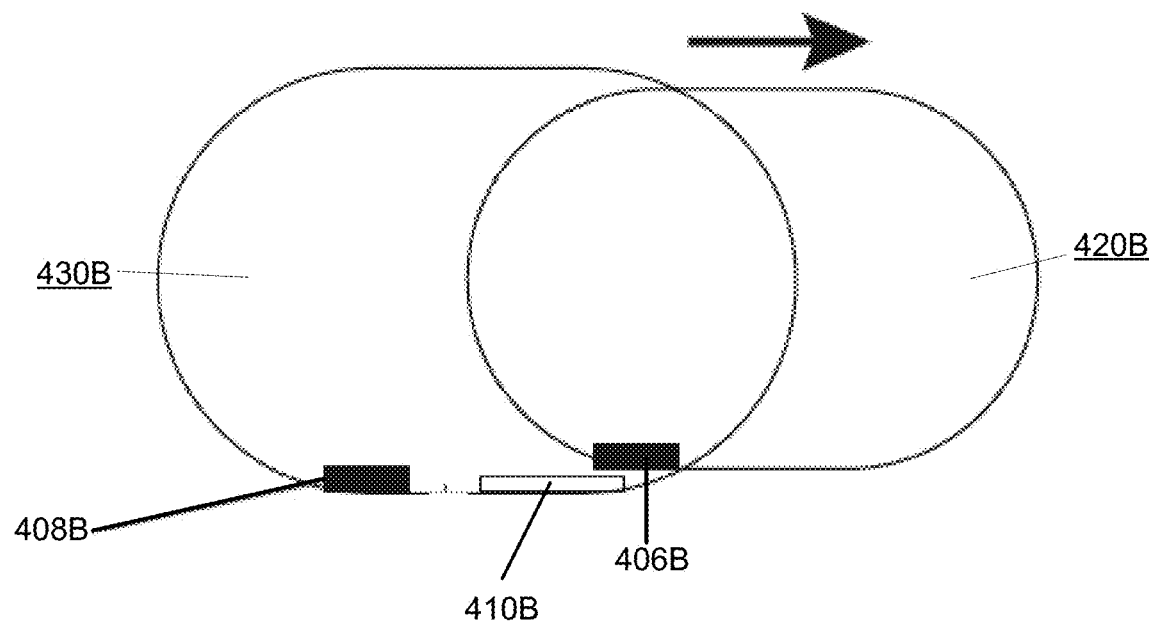
FIG. 4D is an exemplary sensor to detect an event in the health tracking device illustrated in FIG. 4C with a bin open according to another embodiment.

In one embodiment, magnets hold the bins 420 closed by magnets for preventing unintentional opening of the bins. The strength of the magnetic hold (e.g., Gaussian force) is applied to keep bins closed even during light impact and/or sudden changes in velocity of the health tracking device 130. However, the Gaussian force may be weak enough as to not be able to hinder users with dexterity problems from operation. For example, in conjunction with description of FIGS. 4A-B, a second magnet may be used to hold the bin 420 closed. The second magnet is embedded in the bin 420A next to the magnet 402A in the direction toward the back of the bin 420A. A third magnet can be embedded in the outer housing 430A next to the magnetic sensor 404A in the direction toward the back of the bin 420A. When the bin 420A is closed, the attractive force between the second magnet embedded in the bin 420A and the third magnet embedded in the outer housing 430A can be used to hold the bin 420A closed. For another example, as can be seen in FIGS. 4C-D, only a second magnet 408A is used to hold the bin 420A closed. The second magnet 408A is embedded in the outer housing 430A. When the bin is closed, the magnet 406A embedded in the bin 420A attaches to the second magnet 408A embedded in the outer housing 430A for preventing unintentional opening of the bin 420A. The direction of the polarity of the magnets used to secure the position of the bins may be different from the direction of the polarity of the magnets used to activate the sensors in order to reduce unintended activation of sensors due to the magnetic force. In yet another embodiment, a mechanical component (e.g., spring) may be used to prevent the bins from being unintentionally dislodged from the outer housing. In some embodiments, the tactility of the mechanisms can provide a "spring/bounce" feeling to the user of the health tracking device 130.

Figure 6:
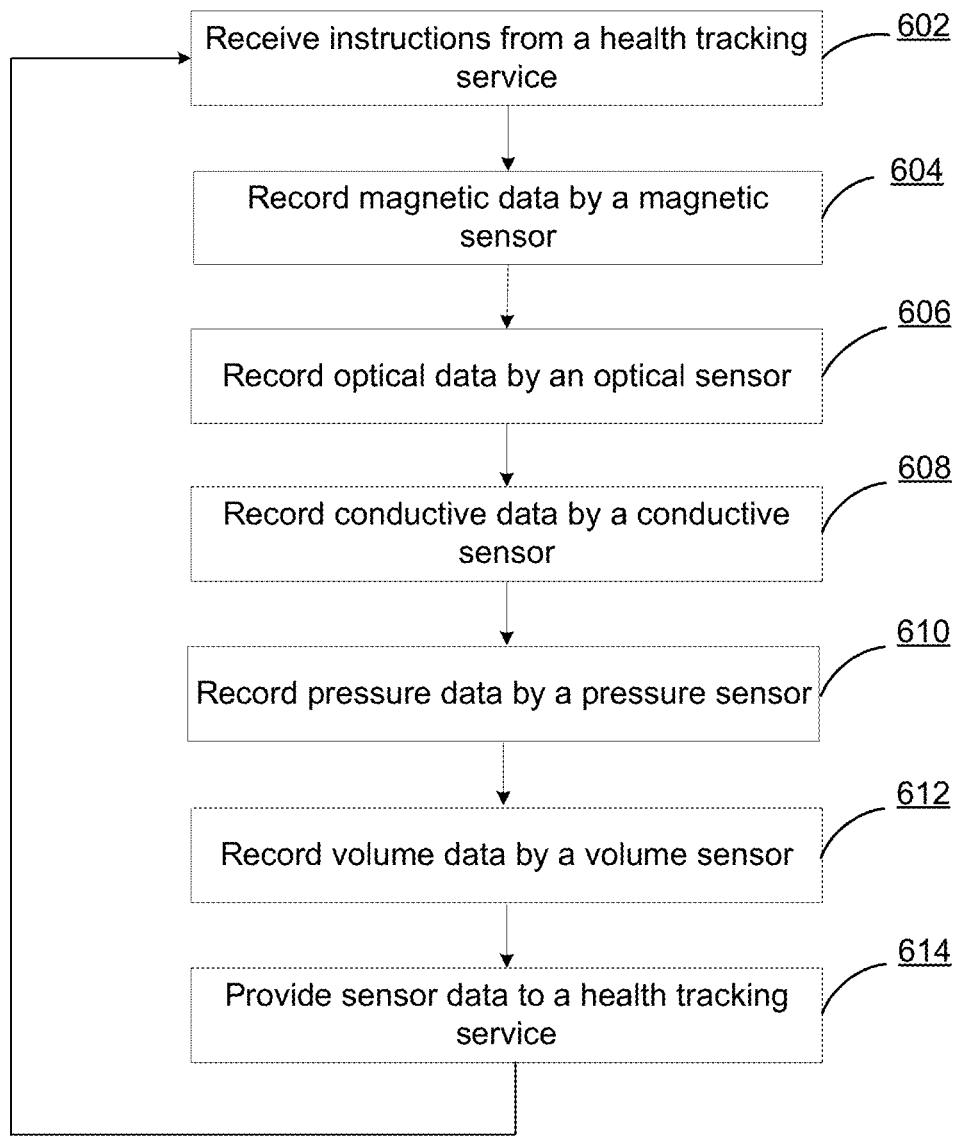
FIG. 6 is an exemplary flowchart illustrating a process for monitoring sensor data associated with a user's medicine consumption related to a prescribed therapeutic regimen or a prescribed medication through various sensors of a health tracking device according to one embodiment.

FIG. 6 is an exemplary flowchart illustrating a process 600 performed by the health tracking device 130 for monitoring sensor data associated with a user's medicine consumption related to a prescribed therapeutic regimen or a prescribed medication through various sensors of the health tracking device 130 according to one embodiment. The process 600 may include different or additional steps than those described in conjunction with FIG. 6 in some embodiments or perform steps in different orders than the order described in conjunction with FIG. 6.

The health tracking device 130 receives 602 instructions from the health tracking service 140, e.g., configurations of the health tracking device 130 and notifications (e.g., warning of accidental or abuse of medicine dispensation, reminder for a user to take medication), as described above. The health tracking device 130 records the state of the switch associated with each bin via recording 604 magnetic data by a magnetic sensor, recording 606 optical data by an optical sensor, and recording 608 conductive data by a conductive sensor. The health tracking device 130 records content consumption via recording 606 optical data by an optical sensor, recording 610 pressure data by a pressure sensor, and recording 612 volume data by a volume sensor. The health tracking device 130 provides 614 sensor data to a health tracking service 140. The health tracking device 130 repeats the steps of 602 to 614 in real time and continuously as long as the health tracking device 130 is used.

In some embodiment, the health tracking device 130 can be integrated into a home kit associated with a smartphone, e.g., an Apple® TV, and is also able to process wireless connection events such as handing off Bluetooth connection from the client device 110A to the Apple® TV without service interruption. For example, the health tracking device 130 can be used in situations where mobile transmission bases or hubs are not present. A user can synchronize data every 30 days or up to 120 event triggers, which are stored on the board memory of the health tracking device 130 and are uploaded at one time.

Health Tracking Service

The health tracking service 140 processes the sensor data collected by the health tracking device 130, provides instructions to the health tracking device 130, and provides recommendations based on the analysis of the sensor data from the health tracking device 130 and historical health data from the external source 160 to the client device 110 for display or to the health tracking device 130 as shown in FIG. 14A and FIG. 14B for display on the display screen (e.g., 1410A in FIG. 14A) of the health tracking device 130. In the embodiment illustrated in FIG. 1, the health tracking service 140 has a database-1 142, a database-2 144, an interface module 146, an analysis module 148, a correlation module 150, a recommendation module 152, a presentation module 154, and an assessment module 156. In alternative configurations, different and/or additional components may be included in health tracking service 140. For example, the health tracking service 140 integrates with various third party hardware or software to provide a comprehensive solution to users of the health tracking service 140. The health tracking service 140 can also integrate the health data analysis into a user's electronic medical records. For another example, the health tracking service 140 can also convert information associated with the user (e.g., data from the health tracking device 130, the software application module 112 of the client device 110, and the external source 160) into behavioral model. Similarly, functionality of one or more of the components may be distributed among the components in a different manner than is described here. For example, some or all of the functionality of the analysis module 148 may be contained within the health tracking device 130.

The database-1 142 stores sensor data received from the health tracking device 130, analysis data generated from the sensor data, correlated data from the correlation module 150, and recommendations from the recommendation module 152. The database-2 144 stores historical health data received from the external source 160, selected historical data from the analysis module analysis 148, analysis data generated from the historical health data, user input data (e.g., user medical profile, user demographics, user's medication information, user's drug prescription and consumption information, and content inventory) from the client device 110, reference data from various sources (e.g., clinical journals, white papers, Internet health websites, nutrition websites or some combination thereof). In some embodiment, only one database can be used to store all the types of data mentioned above.

The interface module 146 facilitates the communication among the client device 110, the health tracking device 130, the health tracking service 140, and the external source 160. In one embodiment, the interface module 146 interacts with the client devices 110 to receive user input data, such as a user's answers to a health risk assessment questionnaire and personal preferences in scheduling appointments with healthcare providers, and stores the received user input data in the database-2 144. The interface module 146 also provides the received user input data to the analysis module 148 and the correlation module 150 for further processing. In another embodiment, the interface module 146 provides any software updates, such as feature updates and security patches, to the software application module 112 of the client device 110 for smooth and secure operation of the medicine consumption monitoring software application.

The interface module 146 receives sensor data recorded by the health tracking device 130 and user historical health data from the external source 160, and stores the received sensor and user historical health data in the database-1 142, and database-2 144, respectively. The interface module 146 also provides the received sensor and user historical health data to the analysis module 148 and the correlation module 150 for further processing, as further explained in conjunction with FIG. 5. The interface module 146 receives instructions associated with the analysis of the sensor data, and provides the received instructions to the health tracking device 130. The interface module 146 also receives recommendations on how to present the analysis data in a user friendly way, and provides the received recommendations to the software application module 112 of the client device 110 for display.

The correlation module 150 correlates sensor data from database-1 142 and selected user historical health data, user input data, reference data from database-2 144, and generates correlated health data. In one embodiment, the correlation module 150 represents the correlated data by an adaptive decision tree. The adaptive decision tree suggests therapeutic regimens, health products, health literature, media and/or services that have a correlation with improving the patient's wellness outcomes. The adaptive decision tree provides the above-mentioned health related suggestions generated by the correlation module 150 via various approaches, e.g., machine learning, statistical analysis, data mining, any other method that estimates the correlation between the received data and the patient's wellness. The health related suggestions can be dynamically updated and is made easily understood by a patient and users in the form of pictures, information graphics, or qualitative sentences that describe what the correlated data means, what may cause the result as well as variables that can impact that result.

In one embodiment, the correlation module 150 applies a trained model to correlates sensor data from database-1 142 and selected user historical health data, user input data, reference data from database-2 144, and generates correlated health data. To train the model, the correlation module extracts feature values from a corpus of training data (e.g., historical user tracking data), the features being variables deemed potentially relevant to whether or not the input data received by the correlation module 150 correlates to each other. Specifically, the feature values extracted by the correlation module 150 include features associated with signals derived from input data. One example of derived signals can be included in a user's medical history, related medical records of his/her family members. Other examples of signals include various health measurements derived from a user's historical health data such as level of activity, ingestion, nourishment, hydration, body weight, biometric data, heart rate, heart rate variability, respiration, blood pressure, quality of sleep and pulse oxygenation.

In some embodiments, the correlation module 150 uses supervised machine learning to train the model for correlating input data. Different machine learning techniques—such as linear support vector machine (linear SVM), boosting for other algorithms (e.g., AdaBoost), neural networks, logistic regression, naïve Bayes, memory-based learning, random forests, bagged trees, decision trees, boosted trees, or boosted stumps—may be used in different embodiments.

In one example, a user of the health tracking server 140 is under XYZ medication. The correlation module 150 is able to retrieve sensor data, user input data, selected historical health data, health reference data associated with the XYZ medication from the two databases (142 and 144). If the medication information from the user input data is to control blood pressure, the correlation module 150 generates the correlated data that is associated with blood pressure control under the XYZ medication, e.g., data from the health tracking device 130, data from the user input, data from a blood pressure monitor, other data from other devices affecting the patient's wellness associated with the XYZ medication. Responsive to the correlation module 150 receiving data, e.g., from a smart utensil and a blood pressure monitor, indicating high sodium intake and high blood pressure, the correlation module 150 interprets the received data with respect to reference data on blood pressure stored in database-2 144 and generates inferences that the increase in blood pressure is correlated to the increased sodium intake. The correlation module 150 generates a decision tree that suggests reducing the sodium intake, or health literature, media, and services that help the patient to control blood pressure or reduce side effects (e.g., lethargy, decreased sensitivity to taste) of blood pressure control medicines, or suggests other recommendation for improving the user's wellness outcomes associated with the consumed medication.

The recommendation module 152 generates recommendations, notifications, and rewards associated with a user's medicine consumption related to a prescribed therapeutic regimen or a prescribed medication. In one embodiment, the recommendation module 152 generates recommendations based on the correlated data represented by the adaptive decision tree discussed above. The recommendation module 152 can also provide additional recommendation for services, products such as alternative dietary supplements to help achieve a desired health result. The notifications include warnings, or information that can be pushed to a network of family, friends, caregivers and/or practitioners associated with the user to help encourage consistency of medicine consumption by the user. Recipients of the notifications may respond to such notifications through the software application module 112 executed on the client devices of the recipients of the notifications, as discussed in conjunction with FIG. 1.

Figure 8:
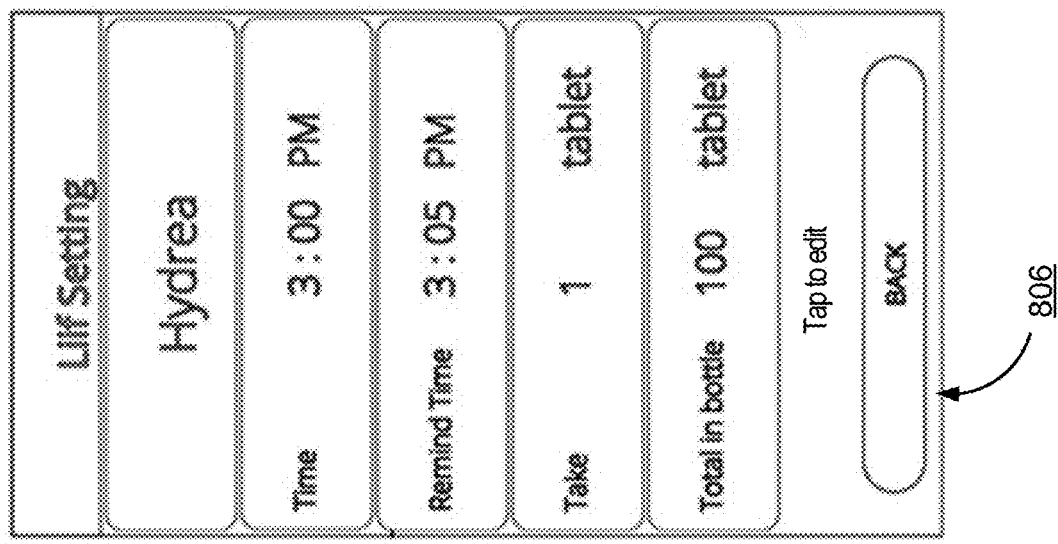
FIG. 8 illustrates examples of graphical user interface to present various types of health tracking information associated with a user's medicine consumption of a drug on a client device according to one embodiment.
Figure 8:
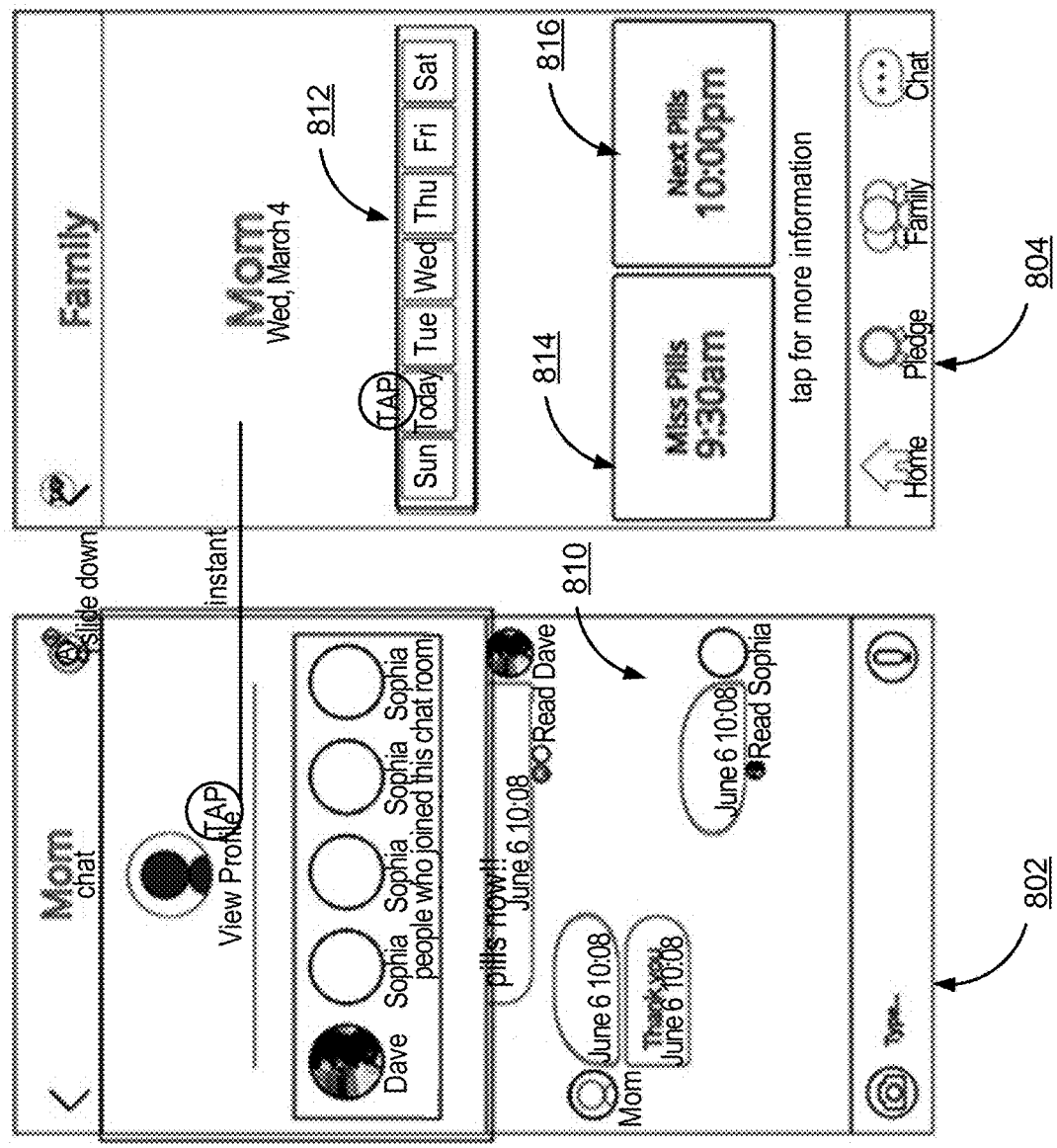

Turning now to FIG. 8, FIG. 8 illustrates examples of graphical user interface to present various types of health tracking information associated with a user's medicine consumption of a drug on a client device according to one embodiment. The examples shown in FIG. 8 include a notification interface 802, a user profile interface 804, and a device setting interface 806. The notification interface 802 shows a patient, i.e., Mom, family members, e.g., Dave, Sophia, and a chat system 810 for communication between the patient and family members. The user profile interface 804 shows current status of the pill consumption of the patient, including days of scheduled pill consumption 812, and time information of missed pills 814 and next pills to take 816. The device setting interface 806 shows current setting of the health tracking device, including the type of the pill (in this example, HYDREA®), current time (3:00 PM), remind time (3:05 PM), amount of pills to take (1 tablet), and pill quantity in a bottle (100 tablets).

The recommendation module 152 generates rewards based on behavior or data collected by the users and provides positive reinforcement for desired behaviors. The desired behavior may result in the user being rewarded with digital currency, coupons, prizes or badges. Multiple users may also compete or pledge to a health challenge over a course of time as a collective effort to provide positive enforcement of desired behaviors. The user that adheres to the therapeutic regimen or a prescribed medication with the highest percentage of adherence may claim a reward that has been agreed upon at the beginning of the competition or pledge.

Figure 12:
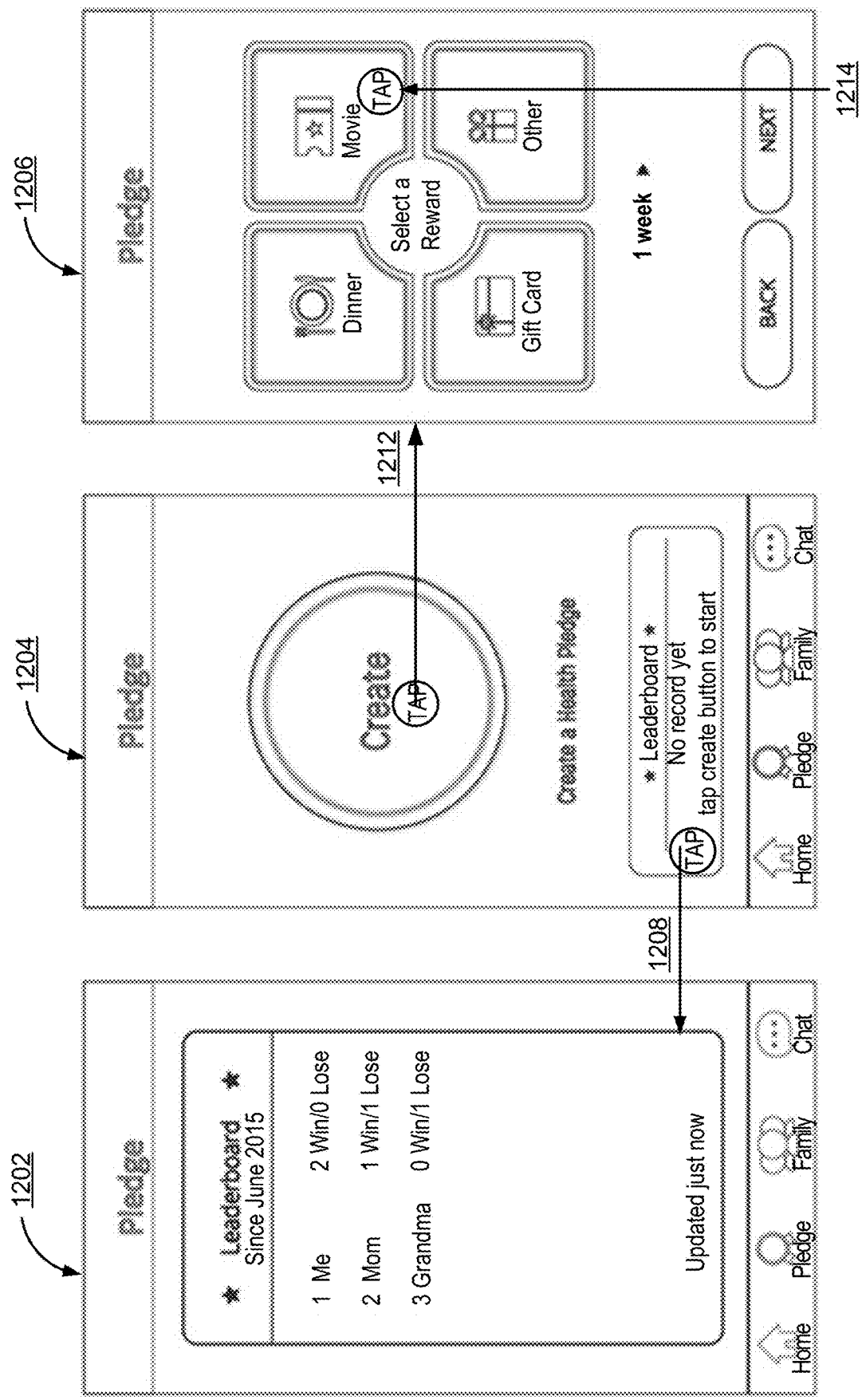
FIG. 12 illustrates an exemplary graphical user interface on a client device to present pledge information according to one embodiment.

FIG. 12 illustrates an exemplary graphical user interface to present pledge information on a client device according to one embodiment. The examples shown in FIG. 12 include a leader board interface 1202, a pledge main interface 1204, and a reward selection interface 1206. By creating a health pledge in the pledge main interface 1204, e.g., clicking a "Create" button 1212, a user is able to select a reward in the reward selection interface 1206, e.g., selecting a movie 1214. By tapping 1208 the leader board 1210 in the pledge main interface 1204, a user is able to see a ranking list showing statistical status of win and lose for participants involved in the leader board interface 1202.

The presentation module 154 generates instructions on how to present the correlated data represented by the adaptive decision tree from the correlation module 150 and recommendations from the recommendation module 152 and provides the presentation instructions associated with the adaptive decision tree and recommendations in a user friendly way to users of the client device 110 for display.

The assessment module 156 tracks adverse reactions of a user/patient through predefined questionnaires. The user's input to the predefined questionnaires may indicate that the user has suffered from or is prone to some health risks that may require an appointment with a healthcare provider. Based on the user's answers to the predefined questionnaires, the health tracking service 140 recommends one or more appropriate family doctors, psychiatrists, therapists, or the like to the user for a personalized health care service.

In one embodiment, the assessment module 156 instructs the software application module 112 of a client device 110 associated with a user to present a predefined questionnaire on a graphical user interface on the client device 110 to user. The user provides his/her answers to the questionnaire through the graphical user interface. The user's answers are received by the assessment module 156 for further analysis.

Turning now to FIG. 15A, FIG. 15A shows an example of a graphical user interface 1510, "Assessment," for presenting a question from a risk assessment questionnaire on a client device for a user according to one embodiment. The question is "How are you feeling (1-5, 1 being the worst)?" The example answer provided by the user 1520 is "2," which indicates that the user is not feeling well.

In response to a user's request for next question, e.g., clicking on "Next" button, a second question, "What is bothering you?" is presented to the user as shown in FIG. 15B. The graphical user interface 1530 shows some commonly known adverse actions associated with a user's medicine consumption of a drug, such as pain, depression and anxiety. The graphical user interface 1530 also allows the user to specify symptoms other than the listed options, and may also allow the user to chat 1550 with a healthcare provider in real time.

The assessment module 156 may provide more questions to further track the user's health and behavioral information associated user's medicine consumption. FIG. 15C shows another example of the graphical user interface 1560 for presenting a question to help identify which part of the user's body is bothering the user. The question is "Where does it hurt?" The user can select from a list of human body parts, such as shoulder, stomach and left chest. In another embodiment, the graphical user interface 1560 may show images representing various human body parts to the user.

Based on the user's answers to the questions shown in FIG. 15A to FIG. 15C, the assessment module 156 may invite the user to schedule an appointment with a healthcare provider through the software application module 112 executing on the client device 110 of the user. FIG. 15D shows another example of the graphical user interface 1580 for inviting the user to schedule a doctor appointment. In response to the user's initiation of scheduling a doctor appointment, e.g., selecting "Yes" to the question of "Do you want to schedule a doctor appointment?" the assessment module 156 instructs the software application module 112 to facilitate the appointment scheduling.

Figure 16:
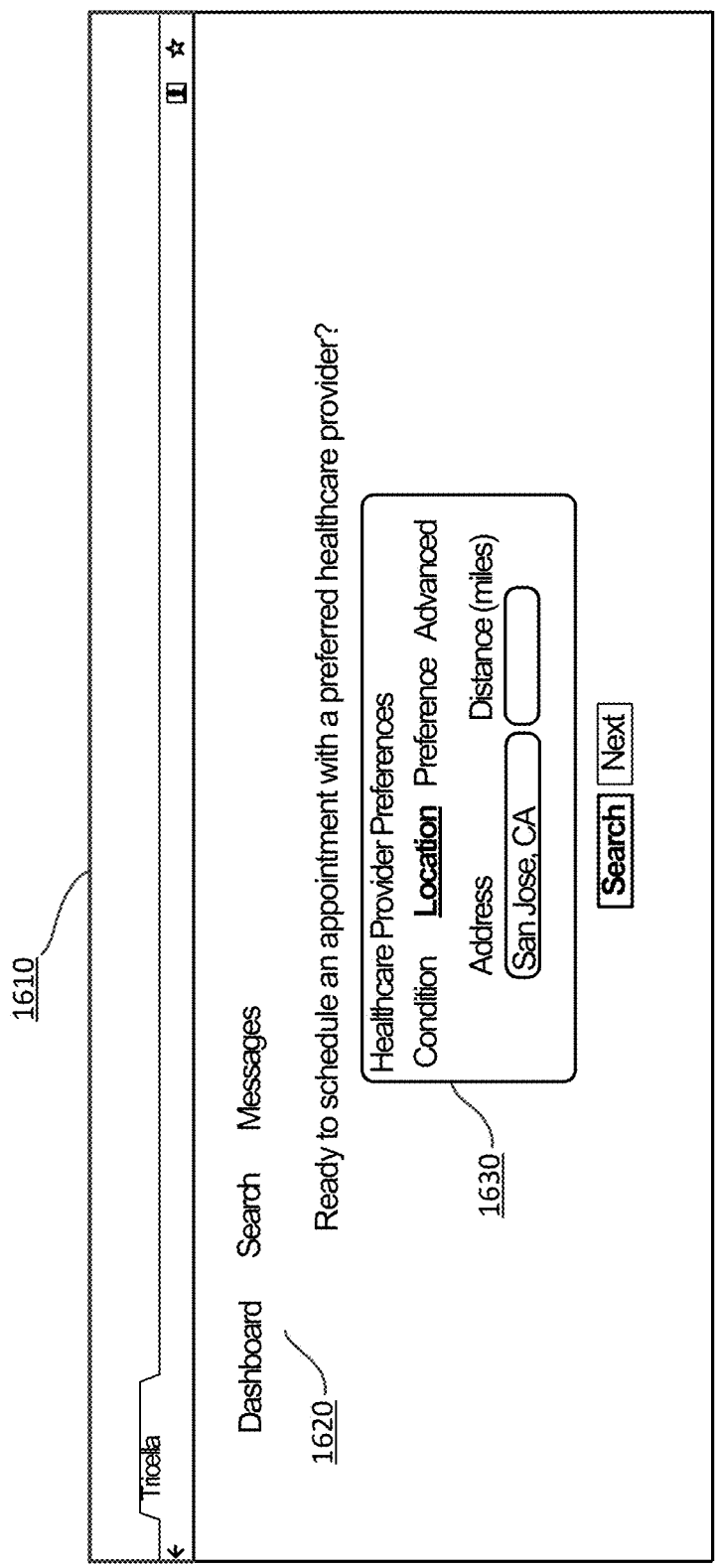
FIG. 16 shows an example of another graphical user interface on a client device for a user to schedule an appointment with a healthcare provider according to one embodiment.

In one embodiment, the software application module 112 on a client device 110 associated with a user receives the instruction from the assessment module 156 and presents a graphical user interface to help the user to customize his/her appointment with a healthcare provider. FIG. 16 shows an example of another graphical user interface 1610 on a client device for a user to schedule an appointment with a healthcare provider according to one embodiment. The user can schedule an appointment with his/her existing physician by providing the physician's information, e.g., name and office address. The assessment module 156 also provides suggestions for locations of one or more healthcare providers based on factors, such as the user's current location, urgency of user's request for appointment, assessment of health risks of the user, historical data of the user's health conditions and the user's preferences.

For example, if the user wants to schedule an appointment with his existing physician at 10'clock in the morning, where the physician is located at destination "A", the user is at location "C" and his caregiver who gives a ride to the user is located at location "B.," the assessment module 156 calculates the distance and estimated travel time based on distance driven, traffic conditions from location B to location C to location A including a time buffer. The assessment module 156 then sends notifications to respective parties when they should "prepare" for the appointment to increase the probability of arriving to the appointment on time.

In addition to track a use's adverse actions associated with his/her drug consumption and facilitate scheduling of doctor appointments, the assessment module 156 may further invite the user to rate their experience with the appointment immediately after the apportionment ends. The assessment module 156 derives the end time of the appointment in various ways, e.g., the end time of the appointment preset by the user, wireless connection to a hands free device (transportation tool) used by the user, and a triangulated position to suggesting the user leaving the facility of the doctor's office.

To provide flexibility for a user to receive his/her health related notifications, the health tracking service 140 can use third party communications platforms, e.g., FACEBOOK™, to send notifications to the user and receive user's input through the third party communications platforms. The health tracking service 140 can also generate health risk assessment questionnaires and respond to uses' input using artificial intelligence and data analysis of data collected by the health tracking service 140 (including data derived from third party integration).

Figure 5:
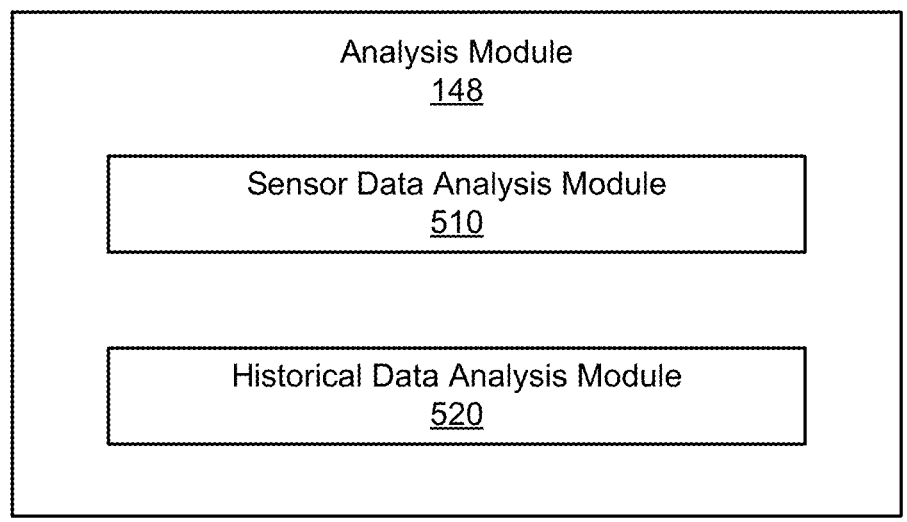
FIG. 5 is a block diagram of an analysis module of a health tracking service to analyze sensor and historical data associated with a user's medicine consumption related to a prescribed therapeutic regimen or a prescribed medication according to one embodiment.

The analysis module 148 of the health tracking service 140 analyzes sensor data and historical health data of a user's medicine consumption related to a prescribed therapeutic regimen or a prescribed medication. FIG. 5 is a block diagram of the analysis module 148 of the health tracking service 140 according to one embodiment. The analysis module 148 shown in the embodiment of FIG. 5 includes a sensor data analysis module 510 and a historical data analysis module 520. Other embodiments of the analysis module 148 can include different and/or additional modules.

The sensor data analysis module 510 retrieves sensor data associated with a user's medicine consumption related to a prescribed therapeutic regimen or a prescribed medication from the database-1 142, user input data from the database-2 144 and analyzes the sensor data. In one embodiment, the sensor data analysis module 510 analyzes the sensor data to derive information about the user's medicine consumption, e.g., date, time and frequency of medicine taken, content dispensation, volumes of consumption, error in dispensing the medicine. For example, the sensor data analysis module 510 determines device status information associated with the status of the switch of each bin of the health tracking device 130 by analyzing the magnetic data from the magnetic sensor 210, optical data from the optical sensor 220, conductive data from the conductive sensor 230, and temporal data from the real-time clock. The sensor data analysis module 510 determines content information of each bin by analyzing optical data from the optical sensor 220, pressure data from the pressure sensor 240, and volume data from volume sensor 250. The content information includes content dispensation, and volumes of consumption by the user of the health tracking device 130.

Upon deriving information about the user's medicine consumption, the sensor data analysis module 510 compares the analysis data associated with the user's medicine consumption and the user input data and determines error in dispensing by detecting a discrepancy between scheduled activities versus actual user behavior. For example, if the analysis data doesn't match the user input data, the sensor data analysis module 510 provides warning of accidental or abuse of medicine dispensation and provides notifications to the user's client device or to other recipients' client devices. For another example, as discussed in FIG. 2, the magnetic sensor 210 records an incident that the switch of a bin is activated or is not activated for a duration that is equal or exceeds the threshold. If the sensor data analysis module 510 detects that the bin is not activated for a duration that is equal or exceeds the threshold, the sensor data analysis module 510 instructs the health tracking device 130 to display a warning. If the sensor data analysis module 510 detects that the bin is activated for a duration that is less than the threshold, the sensor data analysis module 510 removes the opening event recordation, which allows ruling out false triggers of people playing with the health tracking device 130 without intention to consume the medicine.

The sensor data analysis module 510 can also track inventory of contents and sends the information associated with inventory to the recommendation module 152 that generates recommendations based on the tracked inventory. In some embodiments, the sensor data analysis module 510 tracks the content inventory based on the medicine consumption associated with content inventory recorded in the database-1 142. In some embodiments, the sensor data analysis module 510 determines that all the bins are empty or the bins have low inventory of contents. The sensor data analysis module 510 instructs the recommendation module 152 to trigger a push notification to the user's client device as a reminder of low supply, refill, excess supply or suggestions to replenish supply.

The historical data analysis module 520 retrieves a user's historical health data from the database-2 144 and determines portions of the historical health data that are related to the sensor data received from the health tracking device 130. The historical data analysis module 520 selects the portions of the historical health data via various methods, e.g., statistical analysis, machine learning, data mining, other methods that estimates relationship between the received sensor data and the selected historical health data. For example, in response to the sensor data indicating that the user is taking a prescription drug on controlling his high blood pressure, the historical data analysis module 520 retrieves the user's previously prescribed drugs on blood pressure control, number of hospital visits, and number of doctor visits related to his blood pressure and analyzes the his current blood pressure status based on the retrieved historical data.

Figure 7:
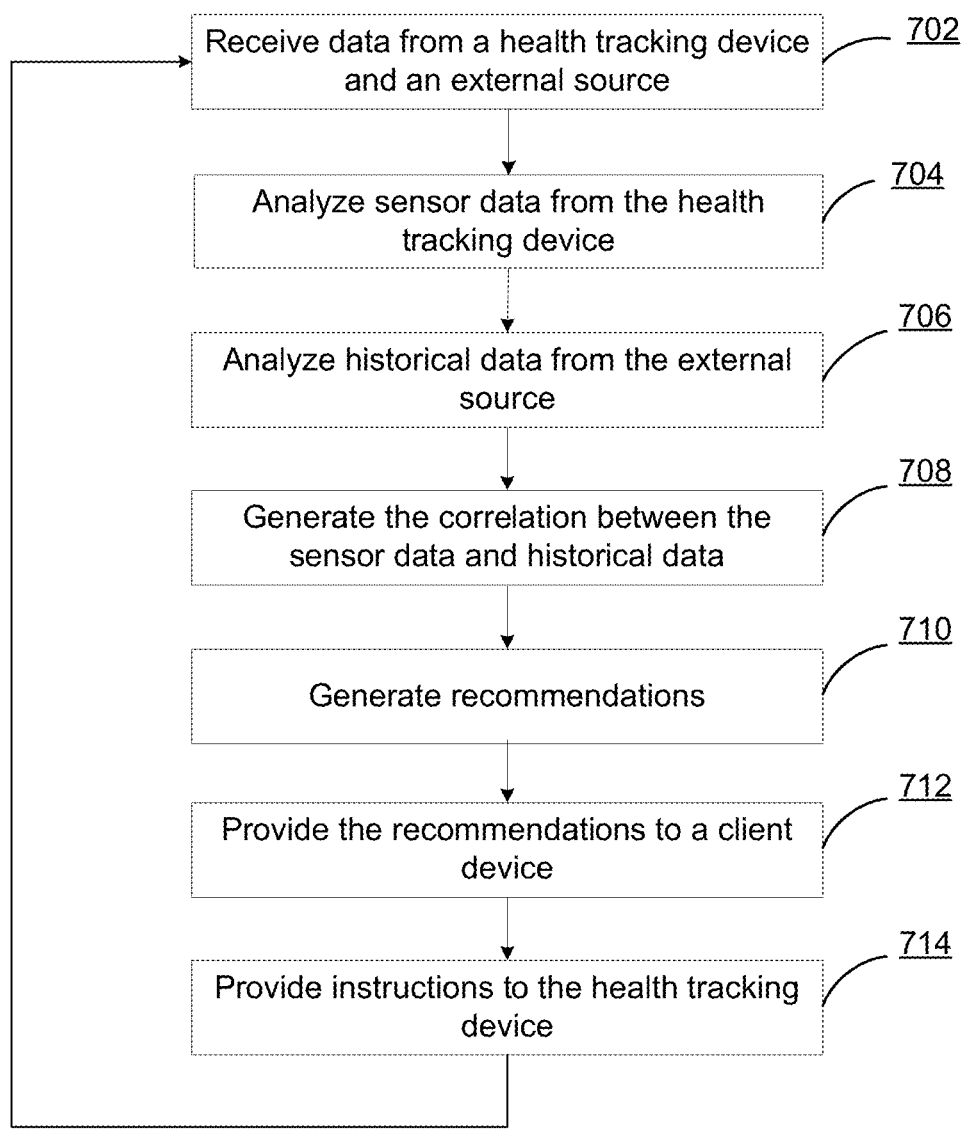
FIG. 7 is an exemplary flowchart illustrating a process for analyzing sensor and historical health data associated with a user's medicine consumption related to a prescribed therapeutic regimen or a prescribed medication by a health tracking service according to one embodiment.

FIG. 7 is an exemplary flowchart illustrating a process 700 performed by the health tracking service 140 for analyzing sensor and historical health data associated with a user's medicine consumption related to a prescribed therapeutic regimen or a prescribed medication according to one embodiment. The process 700 may include different or additional steps than those described in conjunction with FIG. 7 in some embodiments or perform steps in different orders than the order described in conjunction with FIG. 7.

The health tracking service 140 receives 702 a user's sensor data from the health tracking device 130 and the user's historical health data from the external source 160. The health tracking service 140 analyzes 704 the received sensor data to derive the state of each bin of the health tracking device. For example, the health tracking service 140 determines the state of the switch of each bin of the health tracking device 130 by a combination of various sensor data (e.g., magnetic data, optical data, and conductive data). The health tracking service 140 determines whether a bin is open based on the combination of when the magnet in the bin detaches from the magnetic sensor, when the optical sensor detects a displacement of the bin with respect to the outer housing, in which the displacement is equal to or exceeds a threshold value, and when the circuit on a PCB associated with a conductive sensor is completed via the bin's conductive surface. The health tracking service 140 determines content consumption based on a combination of various sensor data (e.g., optical data, pressure data and volume data). For example, the health tracking service 140 determines that the volume of the content in a bin is reducing based on the combination of when the optical sensor detects contents are present in the bin, when the pressure sensor detects contents are present in the bin, and when the volume sensor detects a change in volume of a bin. The health tracking service 140 also determines error in dispensing by detecting a discrepancy between scheduled activities (e.g., scheduled medicine consumption in terms of time and quantity) versus actual user behavior (e.g., sensor data describing the user's actual interactions with the health tracking device 130). For example, if the health tracking service 140 detects an error, the health tracking service 140 provides an instruction (e.g., a warning) to the health tracking device 130 and to the user's client devices 110.

The health tracking service 140 analyzes 706 the user's historical health data received from the external source 160 to select portions of the historical health data associated with the received sensor data. The health tracking service 140 analyzes 708 the correlation between the sensor data and historical health data for generating an adaptive decision tree representing the correlated data. The health tracking service 140 generates 710 recommendations and provides 712 the recommendations to the user's client device or other recipients' client devices. The health tracking service 140 repeats the steps of 702 to 714 in real time and continuously as long as the health tracking service 140 is used.

In some embodiments, the health tracking service 140 is not limited to the embodiments of inventory tracking discussed above. For example, the health tracking service 140 is able to deliver suggestions of replenishment options to the user, e.g., the type of consumables the user may potentially want to replenish the depleting supply with. In some embodiments, the health tracking service 140 is able to communicate with professional care centers or services, logistic systems, or other distribution channels that can automatically fulfill orders for depleting contents. In some embodiments, the health tracking service 140 communicates with professional care services or caregivers for notifying the recipient of completion of a prescribed therapeutic regimen or a prescribed medication, which may trigger another prescribed therapeutic regimen or another prescribed medication.

Example Applications

Figure 9:
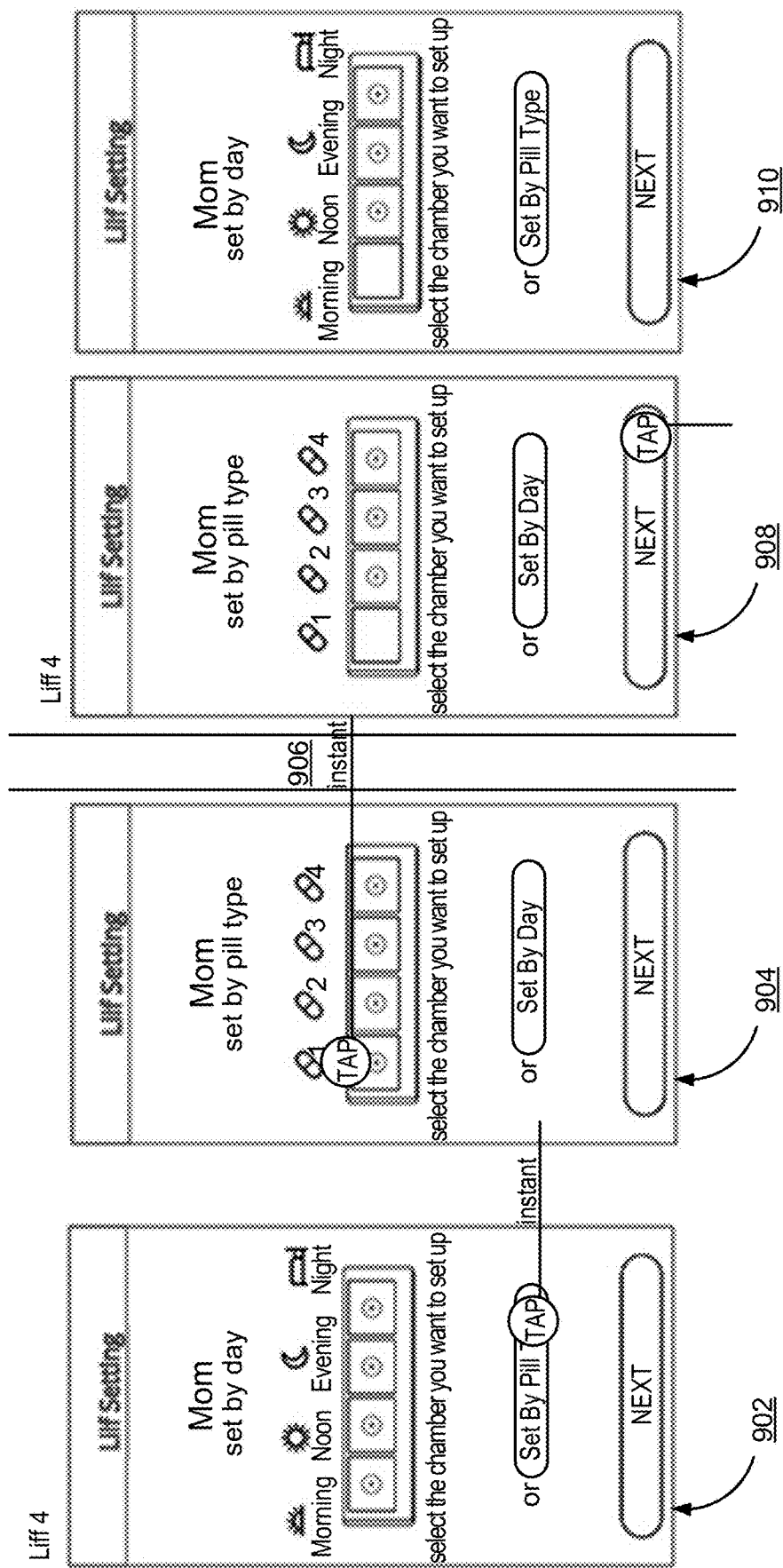
FIG. 9 is an exemplary graphical representation on a display of a client device showing setting information of a 4-bin health tracking device according to one embodiment.

FIG. 9 is an exemplary graphical representation on a display of a client device showing setting information of a 4-bin health tracking device according to one embodiment. The examples shown in FIG. 9 include a day-set setting interface 902, and a pill type-set setting interface 904. The day-set setting interface 902 shows the 4-bin health tracking device is set by periods of a day from morning to bedtime. The pill type-set setting interface 904 shows the 4-bin health tracking device is set by 4 pill types. By taping a selected bin 906, a user can set up each bin according to pill type 908 and day 910.

Figure 10:
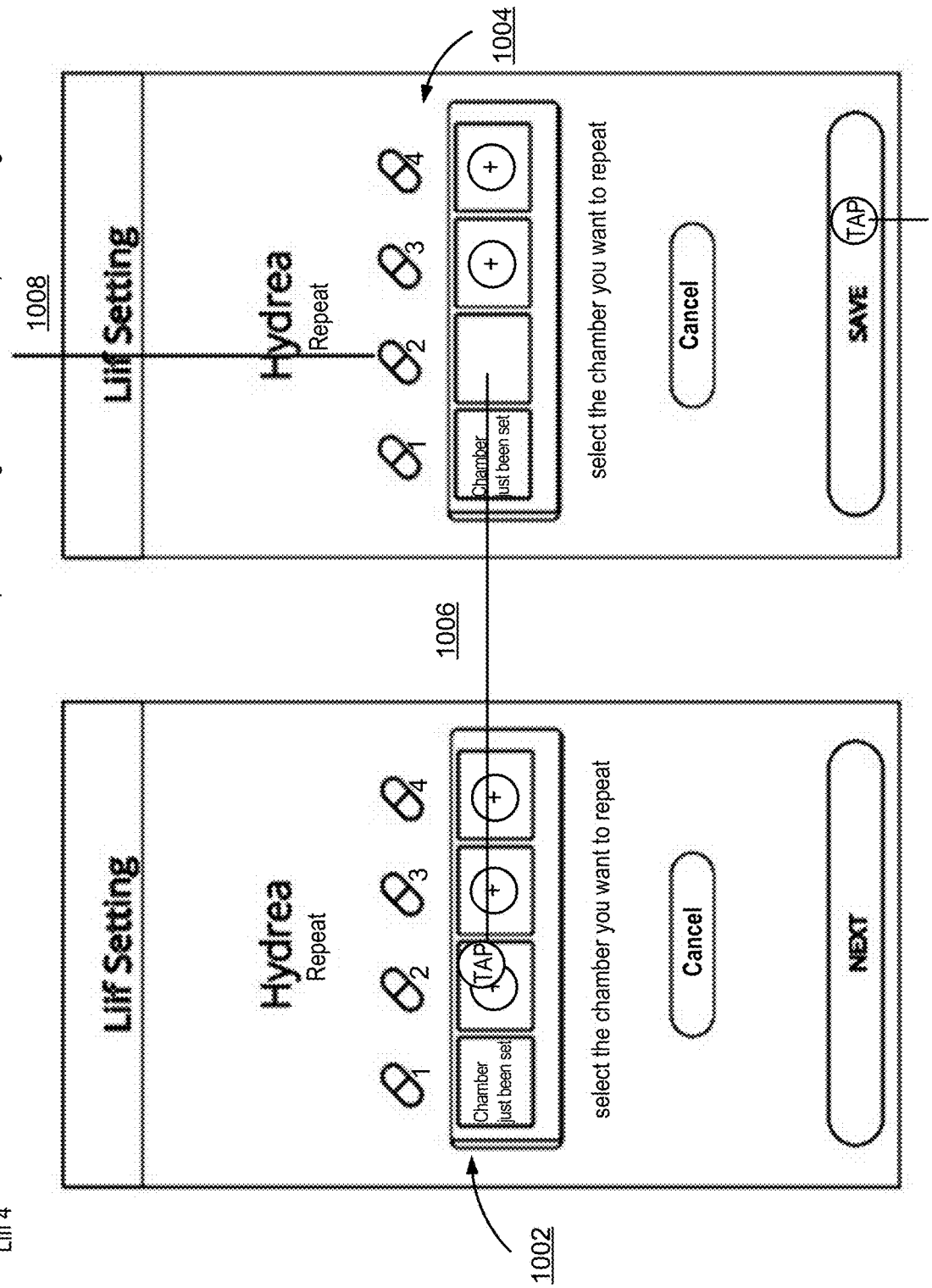
FIG. 10 is an exemplary graphical representation on a client device showing repeated setting information of a 4-bin health tracking device according to one embodiment.

FIG. 10 is an exemplary graphical representation on a client device showing repeated setting information of a 4-bin health tracking device according to one embodiment. The examples shown in FIG. 10 include a setting interface before repeating a setting according to a specific pill type 1002 and a setting interface after repeating the setting according the same specific pill type 1004. By selecting the bin 1006 that a user wants to repeat, the specific bin has the same setting according to the same pill type and pill color changes 1008 to the same color as pervious settings of the bin.

The health tracking device 130 can be set according to a time based scheduling (e.g., time of day, day of week), and the patient can take all the pills in each bin associated with the time schedule. The health tracking device 130 can also be set by pill type. A user can fill each bin with multiples of the same pills, so that each bin can provide multiple days of inventory stored in the health tracking device 130. The software application module 112A in the client device 110A reminds the user which bins are open at a specified time of day, e.g., opening the first, the second and the third bin at 8 am, opening the fourth and the fifth bin at 12 pm, and opening the sixth and the seventh bin at 9 pm. In other embodiments, the health tracking device 130 can be in a tracking only mode and a hybrid schedule set by type and tracking. The tracking only mode is to track how frequently a user takes certain pills, where the users of the health tracking device 130 do not take medication according to a schedule, but take as needed. In the hybrid mode, some of the bins of the health tracking mode can be set to track only while others in the same device is on a schedule by type.

Figure 11:
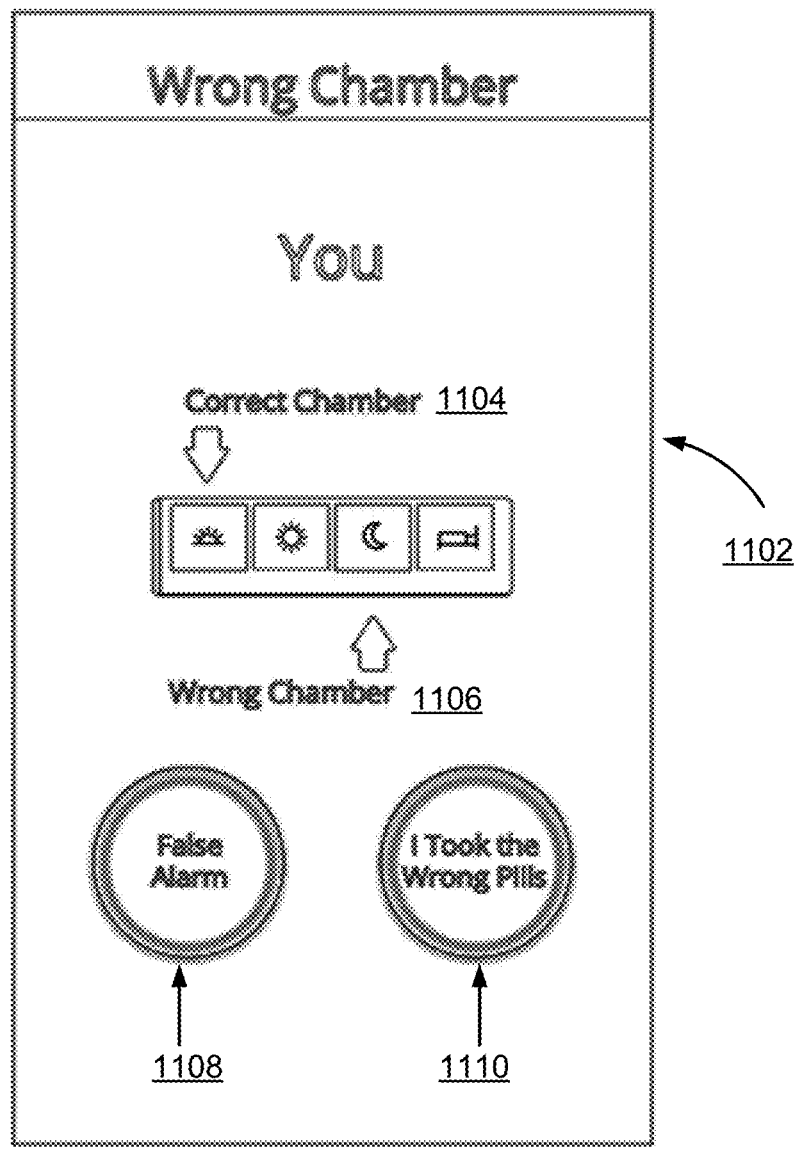
FIG. 11 illustrates an exemplary graphical user interface on a client device to present warning information according to one embodiment.

FIG. 11 illustrates an exemplary graphical user interface on a client device to present warning information according to one embodiment. The example shown in FIG. 11 is a user interface 1102 for showing warning information associated with wrong bin selection. The user interface 1102 shows a correct chamber 1104 that a patient is supposed to take the pill from, a wrong chamber 1106 that a user took the pill from, a false alarm button 1108 allowing the user to cancel the alarm, a notification button 1110 allowing the user to report incidents of taking wrong pills.

In some embodiments, if two or more bins of the health tracking device 130 are pushed, the health tracking device 130 triggers an event indicating refill. For example, the user can confirm if the patient is taking pills from two or more bins or if the patient is refilling the contents. If user confirms that the patient is refilling the contents, the data in the history log does not record the event as "taking pills" or "wrong pills."

Figure 13:
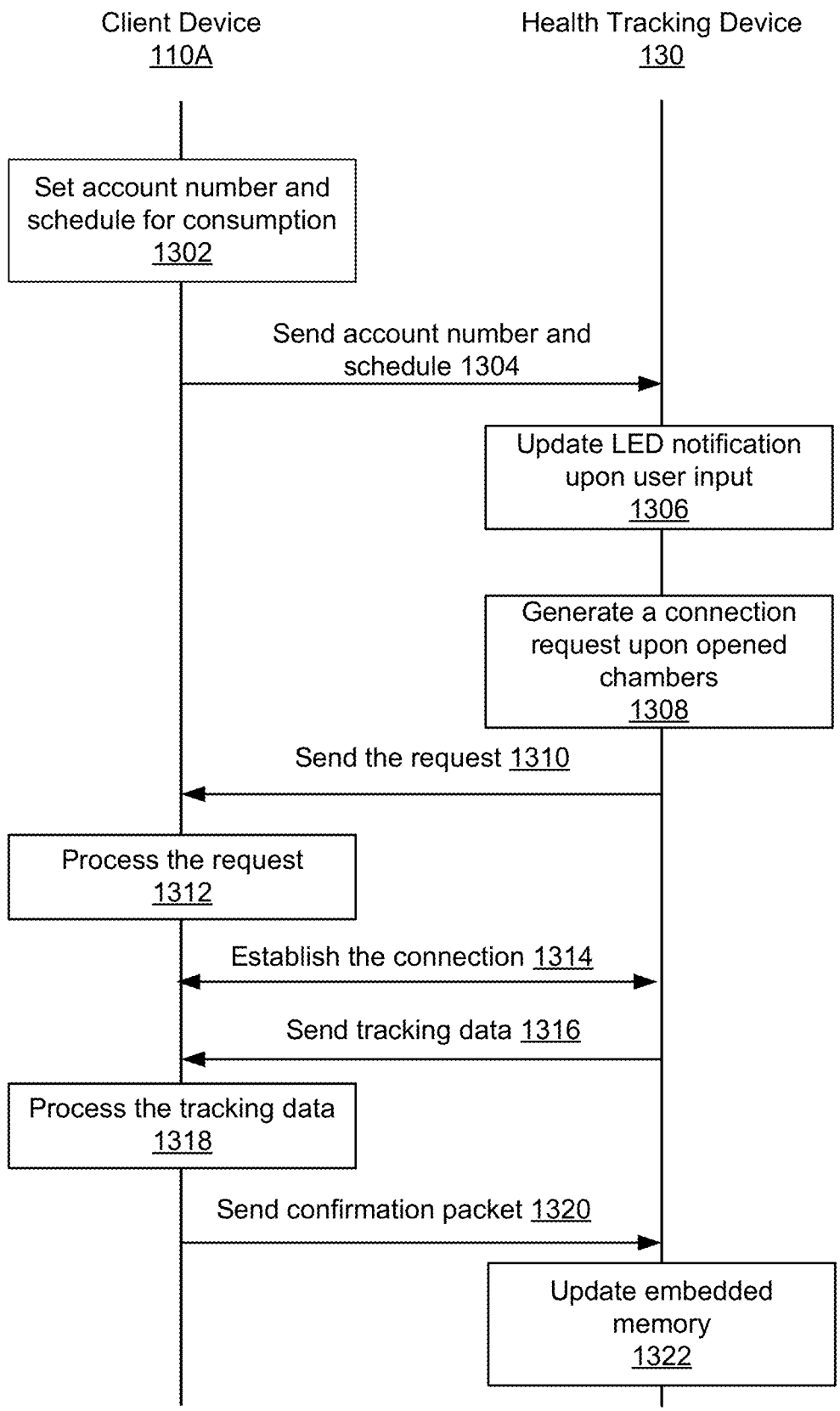
FIG. 13 is an interaction diagram illustrating interactions between a client device and a health tracking device according to one embodiment.

FIG. 13 is an interaction diagram illustrating interactions between a client device 110A (e.g., a smartphone) and a health tracking device 130 (e.g., a pillbox) according to one embodiment. The health tracking device 130 is within the range of the client device 100A for the interactions. A user uses the client device 110A to set 1302 account number with the tracking device and schedules for medication consumption. The client device 110A sends 1304 the account number and schedule information to the health tracking device 130. The user of the client device 110A can turn on or disable LED notification on the tracking device 130, and the health tracking device 130 updates 1306 LED notification upon accordingly. For example, the user of the client device 110A can turn on or disable LED notification of the tracking device 130, which flashes every several seconds for a duration of 2 hours or until the user opens a bin of the tracking device 130.

The health tracking device 130 generates 1308 a connection request to be connected with the client device 110A upon opened bins. For example, the health tracking device 130 generates a broadcast signal as the request for connecting to the client device 110A, only when one or more bins are open. A Normal state of the health tracking device 130 is deep sleep to conserve power. In some embodiments, if the health tracking device 130 does not establish the connection with a threshold time period (e.g., several seconds), the health tracking device 130 returns to a deep sleep state and stores an event of current status of the bins in its onboard memory. The health tracking device 130 does not try to rebroadcast until a next bin is open.

The health tracking device 130 sends 1310 the request to the client device 110A. The client device 110A processes 1312 the request for connecting to the health tracking device 130. The client device 110A establishes 1314 the connection with the health tracking device 130. The health tracking device 130 sends 1316 tracking data to the client device 110A. The client device 110A processes 1318 the tracking data such as notifying the user's care takers to refill the pillbox. In response to receiving the last data packet of the tracking data from the tracking device 130, the client device 110A sends 1320 a confirmation packet to the health tracking device 130 to signal the successful transfer of the tracking data. The health tracking device 130 updates 1322 its board memory such as purging its board memory. In some embodiments, if the health tracking device 130 does not receive the confirmation packet from the client device 110A, the health tracking device 130 continues to store tracking data and status of the tracking device 130 on the board memory.

In some embodiments, the broadcast time of the health tracking device 130 is only long enough to synchronize data that needs to be uploaded to the health tracking device 130. For example, once the client device 110A sends the last packet of the data for uploading to the health tracking device 130 and the last packet is received by the health tracking device 130, the health tracking device 130 goes back to deep sleep. In some embodiments, one or more health tracking devices 130 can be connected to a single client device 110A, e.g., a single user account registered with the client device 110A. The client device 110A is able to detect battery level of the health tracking device 130. In some embodiments, the health tracking device 130 resets to factory default on a battery pull while the health tracking device 130 is still powered on.

General

The foregoing description of the embodiments of the invention has been presented for the purpose of illustration; it is not intended to be exhaustive or to limit the invention to the precise forms disclosed. Persons skilled in the relevant art can appreciate that many modifications and variations are possible in light of the above disclosure.

Some portions of this description describe the embodiments of the invention in terms of algorithms and symbolic representations of operations on information. These algorithmic descriptions and representations are commonly used by those skilled in the data processing arts to convey the substance of their work effectively to others skilled in the art. These operations, while described functionally, computationally, or logically, are understood to be implemented by computer programs or equivalent electrical circuits, microcode, or the like. Furthermore, it has also proven convenient at times, to refer to these arrangements of operations as modules, without loss of generality. The described operations and their associated modules may be embodied in software, firmware, hardware, or any combinations thereof.

Any of the steps, operations, or processes described herein may be performed or implemented with one or more hardware or software modules, alone or in combination with other devices. In one embodiment, a software module is implemented with a computer program product comprising a computer-readable medium containing computer program code, which can be executed by a computer processor for performing any or all of the steps, operations, or processes described.

Embodiments of the invention may also relate to an apparatus for performing the operations herein. This apparatus may be specially constructed for the required purposes, and/or it may comprise a general-purpose computing device selectively activated or reconfigured by a computer program stored in the computer. Such a computer program may be stored in a nontransitory, tangible computer readable storage medium, or any type of media suitable for storing electronic instructions, which may be coupled to a computer system bus. Furthermore, any computing systems referred to in the specification may include a single processor or may be architectures employing multiple processor designs for increased computing capability.

Embodiments of the invention may also relate to a product that is produced by a computing process described herein. Such a product may comprise information resulting from a computing process, where the information is stored on a nontransitory, tangible computer readable storage medium and may include any embodiment of a computer program product or other data combination described herein.

Finally, the language used in the specification has been principally selected for readability and instructional purposes, and it may not have been selected to delineate or circumscribe the inventive subject matter. It is therefore intended that the scope of the invention be limited not by this detailed description, but rather by any claims that issue on an application based hereon. Accordingly, the disclosure of the embodiments of the invention is intended to be illustrative, but not limiting, of the scope of the invention, which is set forth in the following claims.

What is claimed is:

1. A computer-implemented method for tracking health data of a user using a pillbox, the method comprising:
receiving sensor data from one or more sensors embedded in the pillbox in response to a user interaction with a bin of the pillbox, the sensor data recording events based on the user opening or closing one or more bins of the pillbox, wherein the one or more sensors are adjacent to a housing magnet embedded in the pillbox, the housing magnet for exerting a magnetic force to a bin magnet embedded in the bin of the pillbox, the magnetic force to impede the bin from opening;
determining whether the bin of the pillbox was opened based on an analysis of the sensor data;
receiving a plurality of historical health data associated with the user from one or more external sources, the historical health data comprising electronic medical records from various health record sources;
correlating the received sensor data and the plurality of historical health data;

generating an adaptive decision tree based on the correlation of sensor data and the plurality of historical health data;
generating a plurality of health recommendations for the user based on the generated adaptive decision tree; and
providing the plurality of health recommendations to a group of users associated with the user being tracked.

2. The method of claim 1, wherein the user interaction with the pillbox comprises at least of the following actions: opening the bin of the pillbox, and closing the bin of the pillbox.

3. The method of claim 1, wherein analyzing the received sensor data comprises:
analyzing magnetic sensor data detected by a magnetic sensor of the pillbox, the magnetic sensor configured to sense a magnetic field of the bin magnet, and record an event based on a change in the sensed magnetic field of the bin magnet, the event indicating whether the bin of the pillbox was opened or closed.

4. The method of claim 1, further comprising:
providing a notification to a group of users associated with the user being tracked based on status of the one or more bins of the pillbox; and
receiving a response to the notification from at least one of the group of users associated with the user being tracked.

5. The method of claim 4, wherein the response to the notification from a user of the group of users is sent through a touch screen of a user interface of a client device used by the user, and the response is in one of the following formats:
a text message;
a video message;
an audio message;
a voice/video call;
an image; and
a combination of thereof.

6. The method of claim 1, wherein correlating the received sensor data and the plurality of historical health data associated with the user comprises:
applying a trained model to the received sensor data and the plurality of historical health data associated with the user, the model being trained on a corpus of training data using one or more machine learning techniques; and
generating correlated data from the received sensor data and the plurality of historical health data based on the application of the trained model.

7. The method of claim 1, wherein a node of a plurality of nodes of the adaptive decision tree represents a reference to one of therapeutic regimens, health products, health literature, media or services that are relevant to the health of the user.

8. The method of claim 7, further comprising:
providing the plurality of recommendations for display on at least one of a client device associated with the user and a display of the pillbox.

9. A pillbox comprising:
a plurality of bins for storing medicine pills, each of the bins comprising a bin magnet, each bin is configured to be independently opened or closed;
an outer housing for housing the plurality of bins, the outer housing comprising:
one or more housing magnets, each housing magnet configured to attract at least one corresponding bin magnet of a bin when the bin is closed, and
a plurality of sensors, each sensor of the plurality of sensors corresponding to a bin of the plurality of bins, each sensor for capturing sensor data recording events based on a user opening or closing the corresponding bin, wherein the plurality of sensors are adjacent to at least one housing magnet of the one or more housing magnets;
a communication module for transmitting the sensor data to a health tracking service, the health tracking service in response thereto configured to provide at least one of a warning, a recommendation, and a reminder regarding the medicine pills based on an analysis of the transmitted sensor data.

10. The pillbox of claim 9, further comprising a display device to display information received from the health tracking service.

11. The pillbox of claim 9, wherein the plurality of sensors comprise:
a magnetic sensor configured to sense a magnetic field of the bin magnet of a bin, and record an event based on a change in the sensed magnetic field of the bin magnet, the event indicating whether the bin of the pillbox was opened or closed.

12. The pillbox of claim 9, wherein the plurality of bins are configured to open by translating perpendicular to the outer housing.

13. The pillbox of claim 12, wherein the housing magnet prevents the movement of a bin by exerting a force on the bin magnet.

14. The pillbox of claim 12, wherein the plurality of bins are configured to be closed by sliding into the housing in a direction perpendicular to the housing, and to be opened by sliding out of the housing in the direction perpendicular to the housing.

15. The pillbox of claim 9, wherein each bin of the plurality of bins comprises a bin body configured to slide in and out of the outer housing, and wherein the bin magnet of the bin is embedded in the bin body.

16. The pillbox of claim 9, wherein the outer housing comprises:
a plurality of compartments, each compartment of the plurality of compartments configured to receive a corresponding bin of the plurality of bins, each compartment comprising:
a front opening configured to allow the corresponding bin to slide in or out of the outer housing, and
a rear opening for allowing the corresponding bin to be pushed to cause the corresponding bin to slide out of the outer housing.

17. A non-transitory computer readable storage medium configured to store instruction for tracking health data of a user using a pillbox, the instruction when executed by a processor cause the processor to:
receive sensor data from one or more sensors embedded in the pillbox in response to a user interaction with a bin of the pillbox, the sensor data recording events based on the user opening or closing one or more bins of the pillbox, wherein the one or more sensors are adjacent to a housing magnet embedded in the pillbox, the housing magnet configured to exert a magnetic force to a bin magnet embedded in a bin of the pillbox, the magnetic force to impede the bin from opening;
determine whether the bin of the pillbox was opened based on an analysis of the sensor data;
receive a plurality of historical health data associated with the user from one or more external sources, the historical health data comprising electronic medical records from various health record sources;

correlate the received sensor data and the plurality of historical health data;
generate an adaptive decision tree based on the correlation of sensor data and the plurality of historical health data;
generate a plurality of health recommendations for the user based on the generated adaptive decision tree; and
provide the plurality of health recommendations to a group of users associated with the user being tracked.

18. The non-transitory computer readable storage medium of claim 17, wherein the instructions further cause the processor to:
exert a magnetic force, by the housing magnet, to the bin magnet embedded in a bin of the pillbox, the magnetic force to impede the bin from opening; and
analyzing magnetic sensor data detected by a magnetic sensor of the pillbox, the magnetic sensor configured to sense a magnetic field of the bin magnet, and record an event based on a change in the sensed magnetic field of the bin magnet, the event indicating whether the bin of the pillbox was opened or closed.

19. The non-transitory computer readable storage medium of claim 17, wherein correlating the received sensor data and the plurality of historical health data associated with the user comprises:
applying a trained model to the received sensor data and the plurality of historical health data associated with the user, the model being trained on a corpus of training data using one or more machine learning techniques; and
generating correlated data from the received sensor data and the plurality of historical health data based on the application of the trained model.

20. The non-transitory computer readable storage medium of claim 17, wherein a node of a plurality of nodes of the adaptive decision tree represents a reference to one of therapeutic regimens, health products, health literature, media or services that are relevant to the health of the user.

* * * * *